(12) United States Patent
McLaughlin et al.

(10) Patent No.: US 10,311,214 B2
(45) Date of Patent: Jun. 4, 2019

(54) MODE OF ACTION SCREENING METHOD

(75) Inventors: John McLaughlin, Stanford, CA (US);
Zachary Pincus, New Haven, CT (US);
Jim Bernstein, Brisbane, CA (US)

(73) Assignee: RIGEL PHARMACEUTICALS, INC., South San Francisco, CA (US)

( * ) Notice: Subject to any disclaimer, the term of this patent is extended or adjusted under 35 U.S.C. 154(b) by 2533 days.

(21) Appl. No.: 12/985,237

(22) Filed: Jan. 5, 2011

(65) Prior Publication Data

US 2011/0169937 A1  Jul. 14, 2011

Related U.S. Application Data

(60) Provisional application No. 61/335,897, filed on Jan. 12, 2010.

(51) Int. Cl.
*G06F 19/24* (2011.01)
*G06F 19/00* (2018.01)

(52) U.S. Cl.
CPC .......... *G06F 19/707* (2013.01); *G06F 19/706* (2013.01)

(58) Field of Classification Search
None
See application file for complete search history.

(56) References Cited

U.S. PATENT DOCUMENTS

| | | |
|---|---|---|
| H001060 H | 5/1992 | Lazich |
| 5,787,189 A | 7/1998 | Lee et al. |
| 6,759,206 B1 | 4/2004 | Rubin et al. |
| 7,123,764 B2 | 10/2006 | Kirk et al. |
| 2004/0029213 A1 | 2/2004 | Callahan et al. |
| 2005/0233448 A1 | 10/2005 | Oh et al. |
| 2006/0271309 A1 | 11/2006 | Showe et al. |
| 2007/0082327 A1 | 4/2007 | Adams et al. |
| 2008/0195322 A1 | 8/2008 | Altschuler et al. |
| 2009/0010849 A1 | 1/2009 | McGrath et al. |
| 2009/0276384 A1 | 11/2009 | Harris |
| 2009/0285469 A1 | 11/2009 | Callahan et al. |

FOREIGN PATENT DOCUMENTS

| | | |
|---|---|---|
| JP | 2008528975 | 7/2008 |
| JP | 2008539209 | 11/2008 |
| WO | WO2010139697 | 12/2010 |

OTHER PUBLICATIONS

Gama, "Combining classifiers by constructive induction," Machine Learning, vol. 1398, pp. 178-189, 1998.*
Jones, "Predicting Gene Function from Images of Cells," Dissertation, Massachusetts Institute of Technology, 2007.*
Piccardi, "Background subtraction techniques: a review," in Systems, man and cybernetics, 2004 IEEE international conference on, vol. 4, p. 3099-3104, 2004.*
Loo, "Image-based multivariate profiling of drug responses from single cells," Nature Methods, vol. 4, p. 445-453, 2007.*
Shroff, "Wearable Context-Aware Food Recognition for Nutrition Monitoring," Thesis, Carnegie Mellon University, 2008.*
PCT/US11/20262, Notification of Transmittal of the International Search report and the Written Opinion of the International Searching Authority, or the Declaration, dated Mar. 1, 2011, 8pgs.
Boland, et al., "Automated recognition of patterns characteristic of subcellular structures in fluorescence microscopy images", Cytometry, 1998, 33:366-75.
Catalano, et al., ""Discovery and development of an aurora kinase inhibitor clinical candidate using an image-based for measuring proliferation, apoptosis, and DNA content"", Assay Drug Dev Technol., 2009, 7:180-90.
Feng, et al., "Multi-parameter phenotypic profiling: using cellular effects to characterize small-molecule compounds", Nat Rev Drug Discov., 2009, 8:567-78.
Kauvar, et al., "A novel approach to quantitative chemical classification proves useful in drug discovery", Affinity Fingerprinting, Nature Biotechnology, 1995, 13:965-6.
Loo, et al., "Image-based multivariate profiling of drug responses from single cells", Nat Methods., 2007, 4:445-53.
McLaughlin, et al., "Preclinical characterization of Aurora kinase inhibitor R763/AS703569 identified through an image-based phenotypic screen", J Cancer Res Clin Oncol., 2010, 136:99-113.
Perlman, et al., "Multidimensional drug profiling by automated microscopy", Science., 2004, 306:1194-8.
Young, et al., "Integrating high-content screening and ligand-target prediction to identify mechanism of action", Nat Chem Biol., 2008, 4:59-68.
Glick, et al. "Enrichment of High-Throughput Screening Data with Increasing Levels of Noise Using Support Vector Machines, Recursive Partitioning, and Laplacian-Modified Naive Bayesian Classifiers", J. Chem. Inf. Model. 2006, 46, 193-200.
Kei, et al."Elemental Technologies for Genome-based Drug Discovery Test System Using Cultured Live cells", Yokogawa Technical Report English Edition, No. 45, 2008, pp. 27-30.
Carpenter, et al, "CellProfiler; image analysis software for identifying and quantifying cell phenotypes", Genome Biol. 2006;7(10):R100.

* cited by examiner

*Primary Examiner* — G Steven Vanni
(74) *Attorney, Agent, or Firm* — James S. Keddie; Carol L. Francis; Travis Young

(57) ABSTRACT

Certain aspects of this disclosure relate to a screening method. In general terms, the screening assay comprises contacting test cells with a test compound to provide contacted test cells, obtaining values for a plurality of cytological attributes of the contacted test cells, and scoring the cells using the values to provide a likelihood score for at least one of a plurality of classifiers, where the plurality of classifiers are defined using values for cytological attributes obtained from cells that have been contacted with compounds of known mode of action.

20 Claims, 20 Drawing Sheets

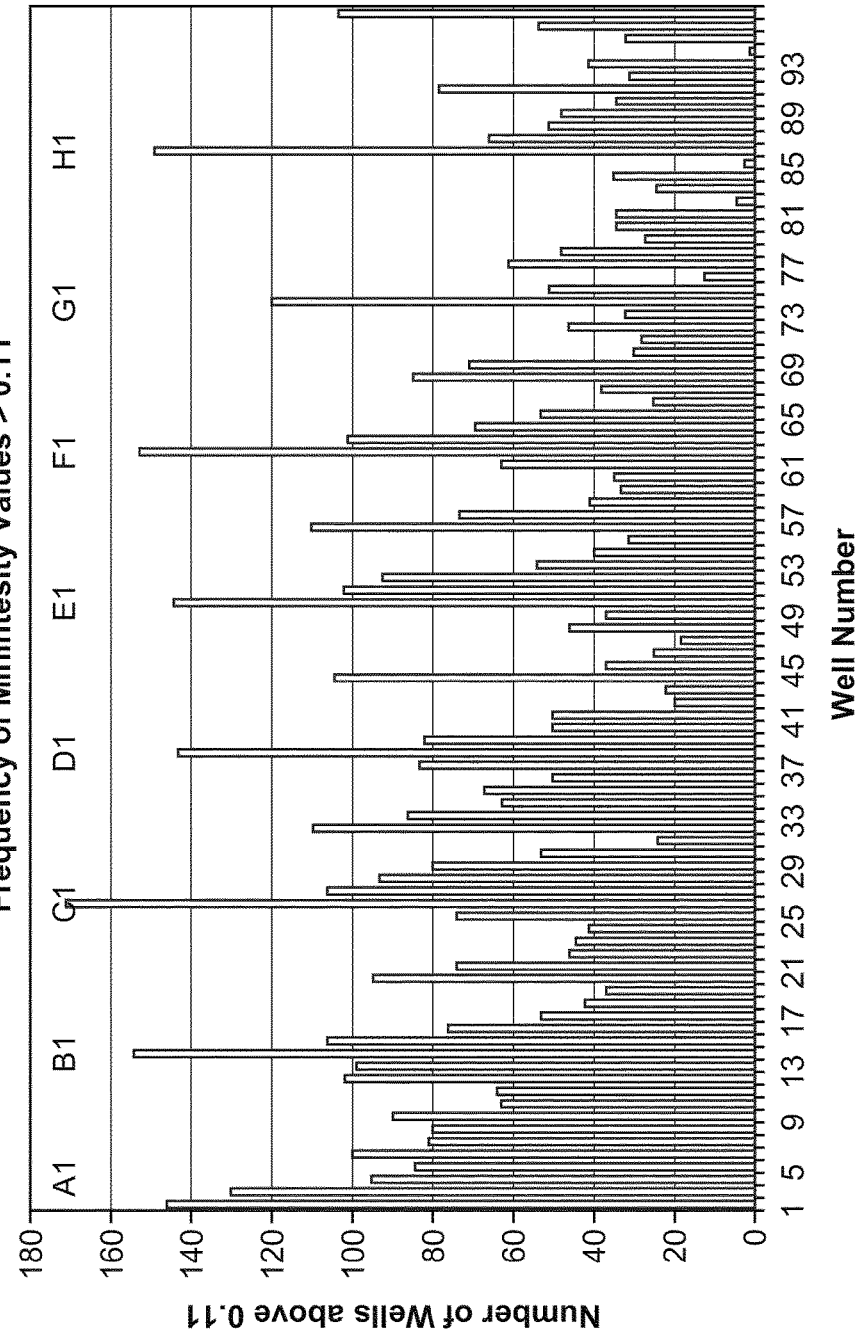
FIG. 2 (Cont. 1)

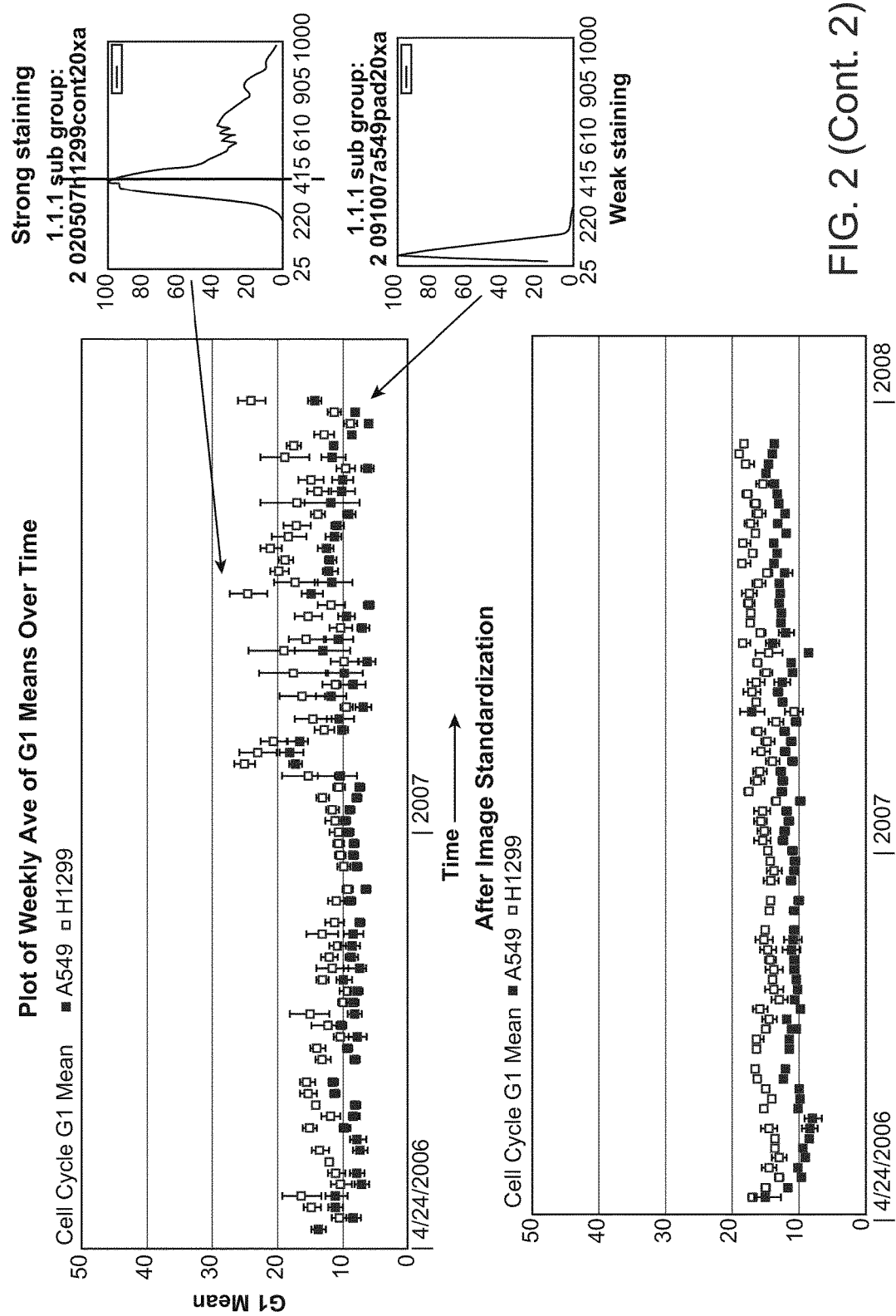
FIG. 2 (Cont. 2)

Image "Standardization" Method

- loop through all the images, segment for the objects, determine the background and the foreground median values for each image and store those values

- loop through the images again, re-segment, then standardize each image according to the formula below:

bkgrndMedian <- query db for the background median value of the current image being processed
foregrnMedian <- query for the average of the dmso control wells foreground median value

```
% get the original image captured by the instrument
img = handles.Pipeline.dapi;
% convert the background median to 0,1 scale
bkgrndMedian = bkgrndMedian / 2^16;
% subtract the background median value
img1 = img - bkgrndMedian;
% convert the foreground median to 0, 1 scale
foregrndMedian = foregrndMedian 2^16;
% divide by the foreground Median value
img2 = img1 / foregrndMedian;
% rescale the image according to the equation:
% new_pixel_value = Offset + old_pixel_value / (Multiple * (1 - Offset)
%where the Offset raises the background slightly above zero
% and the Multiple is the maximum number of times a treatment well could
% reasonably be expected to be above the control wells.
img3 = 0.01 + img2 / (3 * (1 - .01));
% now set everything less than 0 to 0
x = find (img3<0);
img3 (x) = 0;
% now set everything greater than 1 to 1
x2 = find (img3>1);
img3 (x2) = 1;
% now pass that image back to the handle for further processing
handles.Pipeline.dapi = img3;
```

- then measure the new image using the regions found by when segmenting the raw original image

FIG. 3

An Offset of 0.01 and a Multiple of 3 Provide acceptable results
Single Image Histograms
020507h1299cont20xa_A01f01ch0.tif
091007a549pad20xa_A01f01ch0.tif
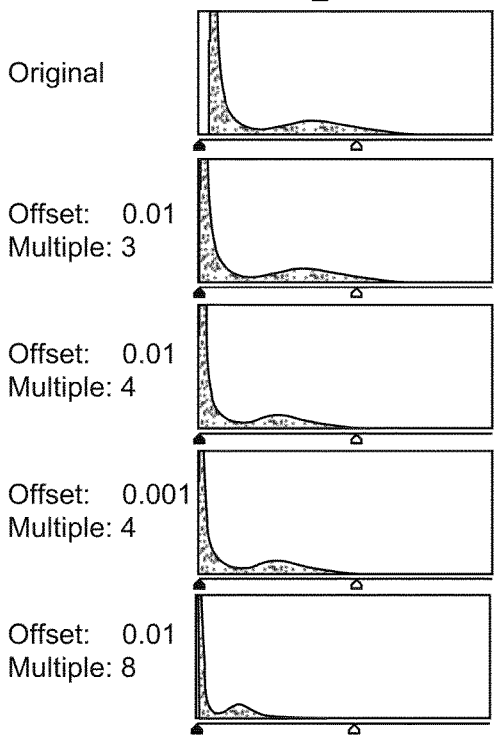
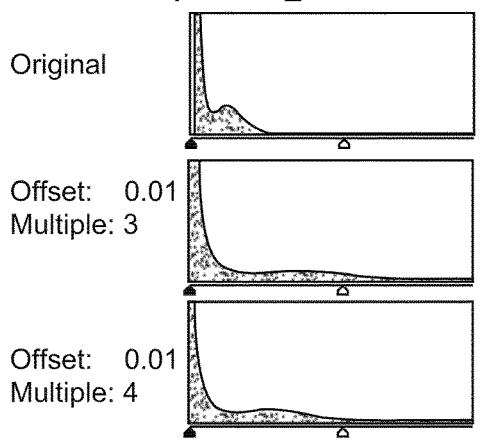
Cell Cycle Plots for DMSO Control
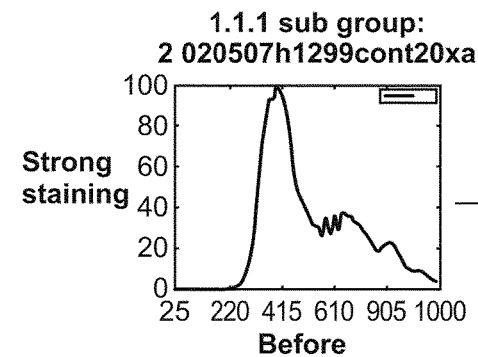
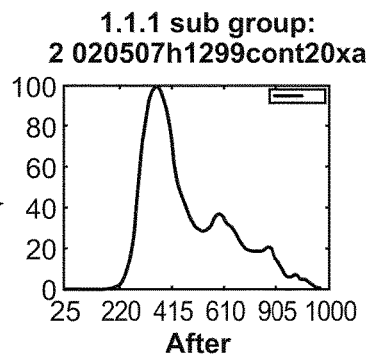
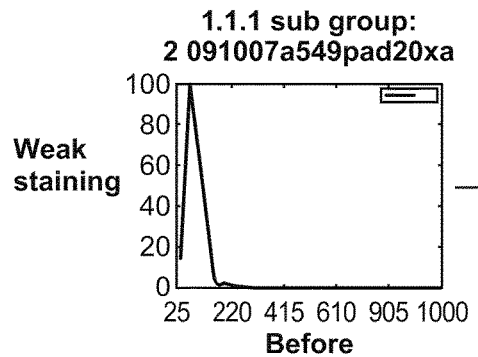
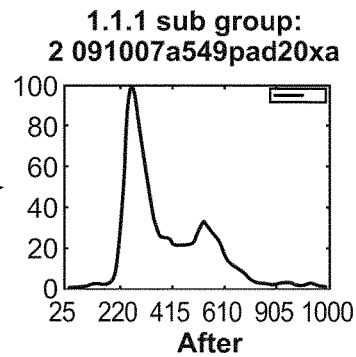
FIG. 4

Step 1: Train Classifier
Cell pixel features are measured then divided into treated or control training sets for classifier training
Step 2: Classify New Data
New data is classified and the output is a binomial distribution of yes and no classifications
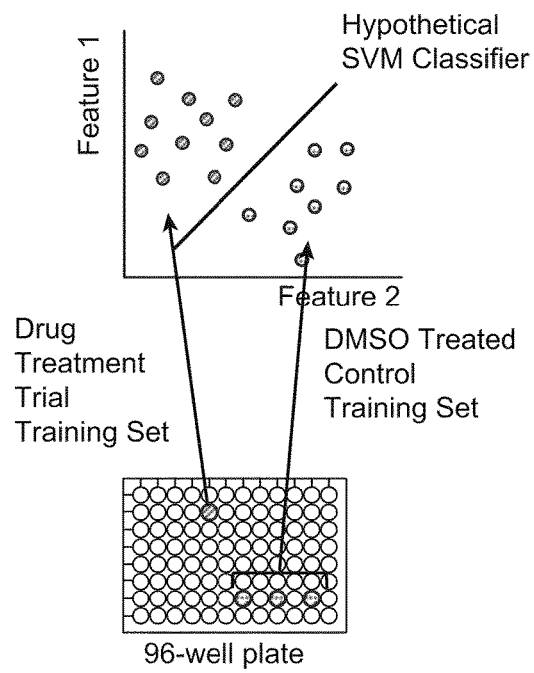
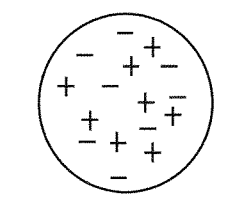
Hypothetical well with yes & no classifications
Step 3: Analysis of Prediction Values
FIG. 8

Well Classification Strategy Uses A Bayesian Approach To Determining a Compound Prediction Value Goal is this:     Use this:

Likelihood ratio:     Bayes Theorem:     Likelihood written in the form of Bayes Theorem:

$$\frac{p(\text{process} = X|\text{data})}{p(\text{process} = Y|\text{data})} \qquad p(\alpha|\beta) = \frac{p(\beta|\alpha) \cdot p(\alpha)}{p(\beta)} \qquad \frac{p(\text{process} = X|\text{data})}{p(\text{process} = Y|\text{data})} = \frac{p(\text{data}|\text{process} = X)}{p(\text{data}|\text{process} = Y)} \cdot \frac{p(\text{process} = X)}{p(\text{process} = Y)}$$

And this to get there:

Binomial Theorem:

$$p(\text{data}|\text{process} = X) = \binom{x+y}{x} a^x (1-a)^y \qquad p(\text{data}|\text{process} = Y) = \binom{x+y}{x} b^y (1-b)^x$$

'x' and 'y' are the actual positive and negative counts for a particular well and 'a' is the performance characteristic of the classifier determined on known, positive control data.

'Prediction values' or Likelihood ratios can range from -3000 to +1000 but typically are around -2000 to +500

FIG. 9

Classifier Performance On New Data Is Assessed By Recall and Precision Metrics Borrowed From Document Retrieval Field Example predictions for compounds classified by a classifier trained to R769 at the EC50+2 concentration

Recall is the number of true positives divided by the total number of elements that actually belong to the positive class Range is 0 to 1 with perfect recall = 1

E.g., 3 positives above threshold divided by 4 total positives = 0.75

Precision the number of items correctly labeled as belonging to the positive class) divided by the total number of elements labeled as belonging to the positive class Range is 0 to 1 with perfect precision = 1

E.g., 3 positives above threshold divided by 6 total positives = 0.5

| Compounds | Predictions |
|---|---|
| AS704216 | 422 |
| R769 | 339 |
| VINBLASTINE | 141 |
| AS703721 | 137 |
| Cytochalasin D | 30 |
| NOCODAZOLE | 14 |
| SU6656 | -14 |
| NSC 663284 | -143 |
| Alsterpaullone | -298 |
| Sunitinib | -395 |
| CyclosporinA | -502 |
| CCT 018159 | -620 |
| Aphidicolin | -709 |
| AG 1024 | -727 |
| AG9 | -765 |
| DNAPKInhibV | -862 |
| SB525334 | -2095 |

Threshold = 0 (between NOCODAZOLE and SU6656)

Positive Controls:
- Target → AS704216, R769
- Similar MOA to Target → VINBLASTINE, AS703721, Cytochalasin D, NOCODAZOLE

FIG. 10

Recall and Precision Results For Some A549 EC50+2 Classifiers

| Cell line | EC50+ Training Compound | Svm name | TP > 0 All TP | All Cmpds | Best Threshold | All Cmpds > Best Threshold | Recall at 0 | Precision at 0 | Precision with best Threshold |
|---|---|---|---|---|---|---|---|---|---|
| A549 | 2 Bortezomib | rmSVM164 | 7 7 | 90 | 190 | 11 | 1.00 | 0.078 | 0.636 |
| A549 | 2 MG132 | rmSVM173 | 6 7 | 64 | 130 | 14 | 0.86 | 0.094 | 0.429 |
| A549 | 2 Camptothecine (S,+) | rmSVM154 | 10 10 | 158 | 210 | 37 | 1.00 | 0.063 | 0.270 |
| A549 | 2 TOPOTECAN | rm9VM156 | 10 10 | 153 | 210 | 22 | 1.00 | 0.065 | 0.455 |
| A549 | 2 Aphidicolin | rm SVM167 | 5 8 | 58 | 220 | 37 | 0.63 | 0.086 | 0.135 |
| A549 | 2 BLEOMYCIN | rmSVM162 | 5 8 | 57 | 160 | 39 | 0.63 | 0.088 | 0.128 |
| A549 | 2 Mitomycin C | rmSVM165 | 8 8 | 113 | 80 | 83 | 1.00 | 0.071 | 0.096 |
| A549 | 2 Paclitaxel | rmSVM244 | 2 2 | 54 | 320 | 7 | 1.00 | 0.037 | 0.286 |
| A549 | 2 NOCODAZOLE | rmSVM247 | 4 6 | 193 | 140 | 104 | 0.67 | 0.021 | 0.038 |
| A549 | 2 VINBLASTINE | rmSVM229 | 6 6 | 176 | 130 | 51 | 1.00 | 0.034 | 0.118 |
| A549 | 2 VINCRISTINE | rmSVM231 | 6 6 | 103 | 60 | 74 | 1.00 | 0.058 | 0.081 |
| A549 | 2 VINPELBINE | rm9VM246 | 6 6 | 165 | 180 | 46 | 1.00 | 0.036 | 0.130 |
| A549 | 2 CYTOCHALASIN D | S025 | 4 4 | 107 | 540 | 7 | 1.00 | 0.037 | 0.571 |
| A549 | 2 LATPUNCULIN A | rmSVM169 | 0 1 | 6 | 0 | 6 | 0.00 | 0.000 | 0.000 |
| A549 | 2 R945769 | rmSVM221 | 9 11 | 48 | 150 | 30 | 0.82 | 0.188 | 0.300 |
| A549 | 2 SU6656 | rmSVM226 | 11 11 | 78 | 340 | 37 | 1.00 | 0.141 | 0.297 |
| A549 | 2 K-252a, Nocardiopsis s | rmSVM224 | 5 5 | 31 | 530 | 10 | 1.00 | 0.161 | 0.500 |
| A549 | 2 Sunitinib | rmSVM253 | 3 3 | 151 | 50 | 69 | 1.00 | 0.020 | 0.043 |
| A549 | 2 NSC 663284 | rmSVM249 | 1 1 | 98 | 3480 | 14 | 1.00 | 0.010 | 0.071 |
| A549 | 2 Met Kinase Inhibitor | rmSVM251 | 3 3 | 243 | 20 | 229 | 1.00 | 0.012 | 0.013 |
| | | | | | | ave | 0.88 | 0.07 | 0.23 |
| | | | | | | stdev | 0.25 | 0.05 | 0.20 |

FIG. 13

Control Compound Validation Set

| Name | Mechanism of Action |
| --- | --- |
| Camptothecin –R181348<br>Topotecan<br>Irinotecan | Topoisomerase I |
| Bleomycin<br>Mitomycin C<br>Aphidicolin –R181351 | DNA Synthesis -Antibiotics |
| Velcade –R142103<br>MG132 | 26S Proteosome |
| R945769<br>SU6656<br>IKK-2 VI<br>K-252a | Kinase –Cause Endoreduplication |
| Latrunculin A<br>Cytochalasin D | Actin Polymerization |
| VinBlastine<br>VinCristine<br>VinRelbine<br>Taxol –R143141<br>Nocodazole | Tubulin Inhibitors |
| NSC 663284<br>Sunitinib -R237664<br>SU 11274 | Miscellaneous Kinase Inhibitors |

FIG. 16

MODE OF ACTION SCREENING METHOD

CROSS-REFERENCING

This patent application claims the benefit of U.S. provisional patent application Ser. No. 61/335,897, filed on Jan. 12, 2010, which application is incorporated by reference herein in its entirety.

BACKGROUND

Drug discovery, as currently practiced in the art, is a long, multiple step process involving identification of specific disease targets, development of an assay based on a specific target, validation of the assay, optimization and automation of the assay to produce a screen, high throughput screening of compound libraries using the assay to identify "hits", hit validation, and hit compound optimization. The output of this process is a lead compound that goes into pre-clinical and, if validated, eventually into clinical trials. In this process, the screening phase is distinct from the assay development phases, and involves testing compound efficacy in living biological systems. Drug discovery efforts often lead to identification of bioactive agents that have unknown or only partially understood systemic effects. Determining how these agents act is usually a labor-intensive process with an uncertain conclusion.

Certain aspects of this disclosure relate to a high-throughput cell-based screening assay that may be employed in drug discovery.

SUMMARY

Certain aspects of this disclosure relate to a screening method. In general terms, the screening method comprises contacting test cells with a test compound to provide contacted test cells, obtaining values for a plurality of cytological attributes of the contacted test cells, and scoring the cells using the values to provide a likelihood score for at least one of a plurality of classifiers, where the plurality of classifiers are defined using values for cytological attributes of cells that have been contacted with compounds of known mode of action. In certain embodiments, the method may involve comparing values obtained from the individual cells in the population to a classifier, determining whether the individual cells are classified or are not classified by the classifier, and calculating the likelihood score using the number of individual cells that are classified by the classifier and the number of cells that that are not classified by the classifier.

Also provided is a microscopy system comprising a device for capturing an image of a population of cells; and a computer, operably linked to the device, comprising programming for: i. analyzing the image to provide values for a plurality of cytological attributes of the cells; and ii. scoring the cells using the values to provide a likelihood score for at least one of a plurality of classifiers, where the plurality of classifiers are defined using values for cytological attributes obtained from cells that have been contacted with compounds of known mode of action.

An image standardization method is also provided. In general terms, this method includes: a) subtracting the median background pixel value of a first image of cells that are present in a first well of a multi-well plate and contacted with a test agent, from the pixel values of the image to provide a second image, and b) dividing the pixel values of the second image by the median foreground pixel values of untreated cells in a second well of the multi-well plate, thereby providing a third image. In this method, the pixel values of the third image may be rescaled. A computer readable medium comprising executable instructions for performing this method is also provided.

A method for providing a phenotypic classifier is also provided. In general terms, this method comprises: a) contacting a first population of cells with a first compound having a first known mode of action to provide a first population of contacted cells; and b) contacting a second population of cells with a second compound having a second known mode of action to provide a second population of contacted cells; c) obtaining values for a plurality of cytological attributes of the first and second populations of contacted cells as well as an untreated population of cells; and d) identifying ranges of values for each of the cytological attributes that, together, distinguish the first population of contacted cells from the second population of contacted cells and the untreated population of cells.

BRIEF DESCRIPTION OF THE DRAWINGS

FIG. 3 provides a method by which an image is standardized.

FIG. 4 illustrates that an offset of 0.01 and a multiple of 3 provides acceptable results.

FIG. 8 schematically illustrates one embodiment of a method.

FIG. 9 illustrates a well classification using a Bayesian approach.

FIG. 10 shows that classifier performance can be assessed by recall and precision metrics.

FIG. 13 is a table of exemplary results.

FIG. 16 is a table showing exemplary compounds and their mechanism of action.

DEFINITIONS

Figure 1:
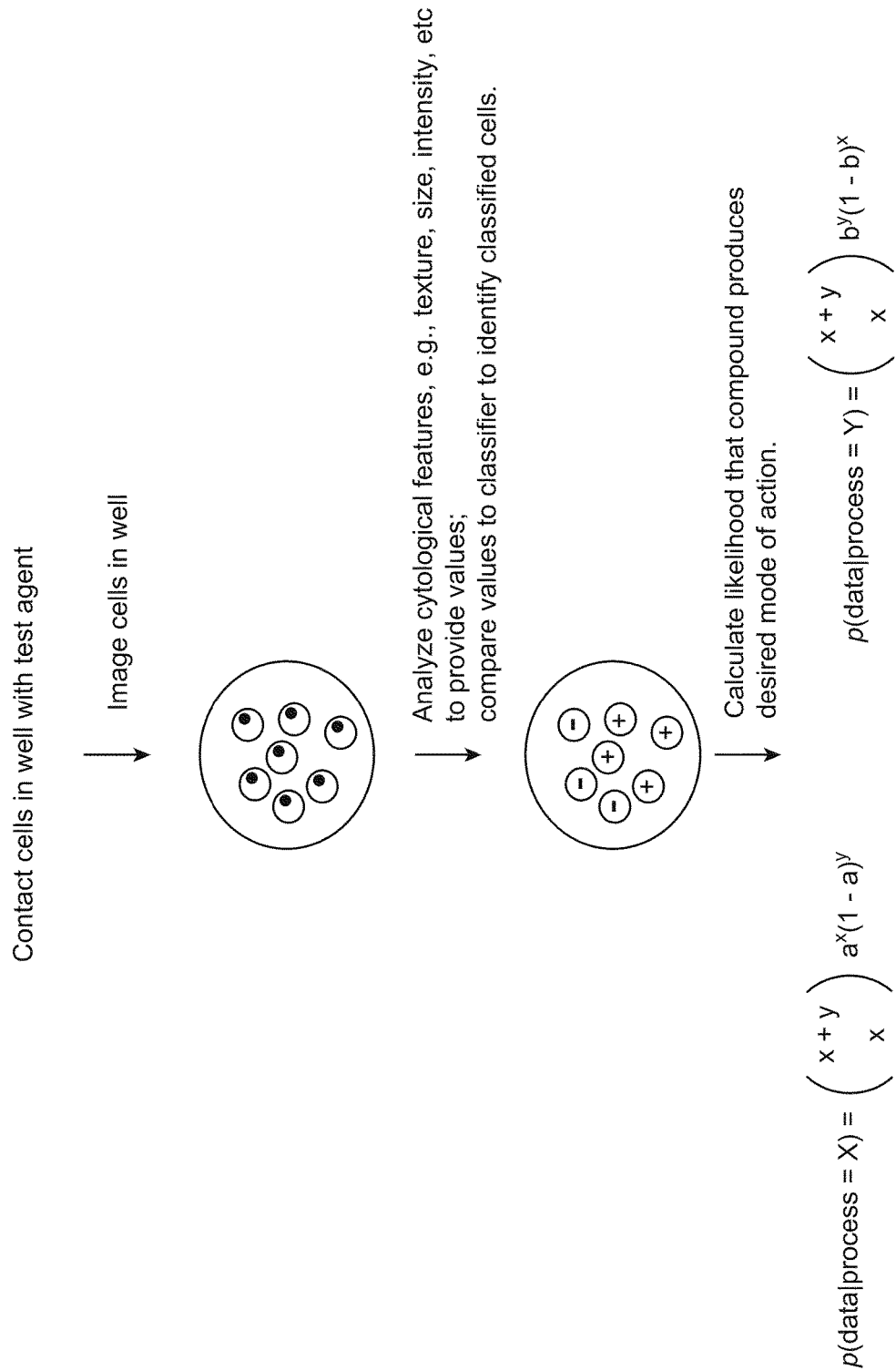
FIG. 1 schematically illustrates one embodiment of a method.

The terms "determining", "measuring", "evaluating", "assessing" and "assaying" are used interchangeably herein to refer to any form of measurement, and include determining if an element is present or not. These terms include both quantitative and/or qualitative determinations. Assessing may be relative or absolute. "Determining the presence of" includes determining the amount of something present, as well as determining whether it is present or absent.

The term "contacting" means to bring or put together. As such, a first item is contacted with a second item when the two items are brought or put together, e.g., by touching them to each other or combining them in the same solution.

Unless otherwise indicated, a cell that is contacted with an agent is a cell in vitro, i.e., a cultured cell. "Introducing into a cell", e.g., introducing a nucleic acid into a cell, is encompassed by the term "contacting".

The terms "candidate agent" and "test compounds" are used to refer to an oligonucleotide, polynucleotide, inhibitory RNA (which may be administered as a shRNA), gene product, polypeptide, small molecule, e.g., up to 2500 Daltons (Da) in size, and any pharmacological compound that is combined with cells in an assay to determine if the agent has a biological activity. In certain cases, a candidate agent may be delivered as a nucleic acid that is transcribed and/or translated to provide the candidate agent, for example, an inhibitory RNA molecule or a polypeptide.

The term "cytological attribute" refers to a phenotypic attribute of a cell or a subcellular structure thereof, e.g., a cell's nucleus or an actin staining pattern. Size, staining intensity, shape, elipticity and texture are examples of cytological attributes. The term "cytological attribute" may be referred to as a "phenotypic attribute", "parameter", or "feature" in certain other publications (e.g., Young et al, Nature Chemical Biology 2007 4: 59-68; Feng et al, Nature Reviews 2009 8: 567-578). Cytological attributes may be identified by staining. Many examples of cytological attributes are described in reference cited below.

With reference to a "cytological attribute", the term "value" (e.g., as in the phrase "obtaining values for a plurality of cytological attributes") refers to a numerical evaluation of (e.g., a measurement) of a cytological attribute or a statistical derivative (e.g., the average, median or variation in) of a plurality of numerical evaluations. Exemplary values for cytological attributes include size measurements for either the cell or nucleus of a cell, which can include measurements of area, length, width, diameter, etc., total, median or the variation in intensity of staining of the cell or nucleus thereof, irregularity in shape, degree of elipticity and texture, etc. In general terms the number of values obtained for a single cell may be in the range of 20 to 500 or more, depending on the desired level of complexity.

The term "classifier" refers to a collection of ranges of values of cytological attributes that, together, define a phenotype produced by contacting a cell with a bioactive agent. If the bioactive agent has a defined mode of action, the phenotype of the contacted cell, and therefore the classifier, defines the mode of action of the bioactive agent. For example, a particular phenotype that defines a mode of action of a bioactive agent may be defined using ranges of over 100 different values, which ranges distinguish the phenotype of a contacted cell from the phenotype of control cells or other cells that are contacted with other bioactive agents that have a different mode of action.

The term "likelihood score" refers to an estimate of the certainty of a prediction. A likelihood score is not binomial. Rather it is a continuously variable number, which may be a ratio, an odds or a scaled number, e.g., a percentage.

The term "Bayesian theorem" is a theorem in which one conditional probability (such as the probability of a hypothesis given observed evidence) depends on its inverse (in this case, the probability of that evidence given the hypothesis). Bayesian theory is described in Howson (*Scientific Reasoning: The Bayesian Approach* 1993 Open Court) and Jaynes (*Probability theory: the logic of science* 2003. Cambridge University Press), which are both incorporated by reference herein.

The term "profile of likelihood scores" refers to a set of likelihood scores for different classifiers, where each likelihood score provides an estimate of a certainty of the prediction.

The term "mode of action" refers to a specific biochemical interaction through which a bioactive agent produces a pharmacological effect.

The term "pixel value" refers to the intensity of pixel. For example, for an image captured by a 16-bit imaging system, a pixel value may be a natural number in the range of 0 to 65,536. A pixel value may be re-scaled to fall in the range of 0-1, e.g., by dividing the pixel value by 65,536 in the case of a 16-bit image.

The term "plurality" refers to two or more, e.g., at least 2, at least 5, at least 10, at least 50, at least 100, at least 1,000, up to 10,000 or 100,000 or more.

With reference to an image of cells, the term "background" refers to those parts of the image that correspond to areas between cells.

With reference to an image of cells, the term "foreground" refers to those parts of the image that are within the outer perimeter of each cell in the image.

DESCRIPTION OF EXEMPLARY EMBODIMENTS

Before the present subject invention is described further, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a cell" includes a plurality of cells, reference to "a candidate agent" includes reference to one or more candidate agents and equivalents thereof known to those skilled in the art, and reference to "a value" includes reference to values that are averaged across two or more samples, and so forth. It is further noted that the claims may be drafted to exclude any optional element. As such, this statement is intended to serve as antecedent basis for use of such exclusive terminology as "solely", "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

With reference to FIG. 1, the method generally includes contacting cells grown in culture with a test agent, and then imaging the cells to provide an image. The cytological attributes of the cells in the image are analyzed to provide a plurality of values for each of the cells, and the values for each cell are compared to a classifier that either does or does not classify the cell. This step, for each population of cells, produces a binomial output that indicates whether the individual cells in the population are classified or not classified by the classifier. The classifier is defined using values for the same cytological attributes as analyzed for the test cells, except that the values for the cytological attributes are obtained from cells that have been contacted with compound having a known mode of action. The classifier distinguishes the phenotype of cells exposed to a biological agent with a known mode of action from other cells. Using the binomial output, as well as an estimate of the performance of the classifier using positive controls, a likelihood score that the test agent has the same mode of action as the agent having a known mode of action is calculated. The method may be employed in a "high-throughput" manner in which multiple populations of cells are grown in the wells of a multi-well plate, there is a control on every multi-well plate (e.g., a population of cells that are not contacted with any agent), and the imaging and analysis is done using an automated microscope system.

The following publications are incorporated by reference herein for their description of exemplary assay steps and hardware that could be employed in the subject method: Catalano (*Discovery and Development of an Aurora Kinase Inhibitor Clinical Candidate Using an Image-Based Assay for Measuring Proliferation, Apoptosis, and DNA Content Assay* Drug Development Technologies 2009 7: 105-109), McLaughlin (*Preclinical characterization of Aurora kinase inhibitor R763/AS703569 identified through an image-based phenotypic screen* J. Cancer Res. Clin. Oncol. 2009 136: 99-113; Boland (*Automated Recognition of Patterns Characteristic of Subcellular Structures in Fluorescence Microscopy Images* Michael Cytometry 1998 33: 366-375); Perlman (*Multidimensional Drug Profiling By Automated Microscopy* Science 2004 306: 1194-8), Loo (*Image-based multivariate profiling of drug responses from single cells* Nat. Methods 2007 4: 445-53); Young (*Integrating high-content screening and ligand-target prediction to identify mechanism of action* Nat. Chem. Biol. 2008 4: 59-68; Feng et al (*Multi-parameter phenotypic profiling: using cellular effects to characterize small-molecule compounds* Nat. Chem. Biol. 2008 4:59-68) and Kauvar (*Affinity Fingerprinting A novel approach to quantitative chemical classification proves useful in drug discovery* Bio/Technology 1995 13, 965-966). These publications are incorporated for disclosure of, in particular: general cell culture methods, bioactive agents, staining methods, cell imaging methods, cytological attributes and methods for measuring the same, image processing methods and downstream data processing methods.

Certain aspects of the method are described in greater detail below.

Standardization Method

This disclosure provides an image standardization method. In this method, an image of cells in a well of a multi-well plate is used to standardize an image of cells in a different well of the same multi-well plate. In this method, a first population of cells is cultured in a test well of a multi-well culture plate and contacted with a test agent. An image of those cells is then standardized against an image of a population cells grown in a control well that is present on the same plate as the test well. In this method the values of the pixels that make up the image of the first population of cells are adjusted. First, the image of the test cells (i.e., the "first" image) is analyzed to identify foreground and background pixels, and the median intensity of the background pixels is calculated. The median intensity of the background pixels of the first image is subtracted from the pixel values of the first image to provide a second "background-subtracted" image. The pixel values for the second image are then divided by the median foreground pixel values of an image of untreated cells in a second well of the same multi-well plate, thereby providing a third image. In certain embodiments, the cells in the test well are contacted with a test agent that is present in an inert excipient, e.g., water, ethanol or a dipolar aprotic solvent such as DMSO, and the cells in the control well are contacted with only the inert excipient. In one embodiment, the cells in the test well are contacted with an agent dissolved in DMSO, and the cells in the control well are contacted with DMSO alone. As would be readily apparent, results from multiple control wells may be employed in this method, e.g., by averaging their results.

In particular embodiments, the pixel values that make up the third image may be further adjusted so that they are above zero, and so that they are approximately in the same scale as for other images. In these embodiments, the pixel values that make up the third image may be rescaled to produce a scaled image in which the pixel values equal an offset+pixel values for the third image value/multiple*(1-offset), where the offset raises the values for all of the pixels in the third image above zero and the multiple is at least 1. In one embodiment, the offset is below 0.1, and the multiple is at least 1 (e.g., in the range of 1-10). Such a method is illustrated in FIG. 3.

The method may be repeated for images of cells in other wells of the multi-well plate. In particular embodiments, at least some of the cells in the other wells have been contacted with further test agents. The method may be used to standardize every test well of a multi-well plate prior to further processing of the images of the test wells.

A computer readable medium comprising executable instructions for performing this method is also provided. Such a computer readable medium is described in greater detail below.

Method for Defining a Classifier

Also provided herein is a method for defining a phenotypic classifier, which, as noted above, is a collection of ranges of values of cytological attributes that, together, define a phenotype produced by a bioactive compound. Classifiers, when used in a screening method such as that described below, not only allow cells to be distinguished from one another based on their phenotype, but also identify a cell's phenotype as being similar or identical to that of the cells that were used to define the classifier. Once such a "phenotypic fingerprint" of a bioactive agent having a known mode of action has been defined, agents can be screened for those that produce a similar fingerprint. Thus, a compound that has a mode of action that is similar to that of a compound with a known mode of action can be identified.

This method involves identifying ranges of values for a plurality of cytological attributes for cells that have been exposed to a first bioactive agent, e.g., an agent that has a defined mode of action, where the ranges of values distinguish those cells from other cells that have been exposed to excipient alone and/or cells exposed to other bioactive agents that produce a different phenotype to the first bioactive agent, e.g., agents that have a different mode of action to the first bioactive agent.

In certain embodiments, the first step of the method involves contacting a first population of cells with a first compound having a first known mode of action to provide a first population of contacted cells, and contacting a second population of cells with a second compound having a second known mode of action to provide a second population of contacted cells. Values for a plurality of cytological attributes for the first population of contacted cells, the second population of contacted cells and for control cells that have been exposed only to excipient are obtained from images of the cells, and ranges of values for each of the cytological attributes that, together, distinguish the population of contacted cells from the second population of contacted cells and the untreated population of cells are identified. In this method, the populations of cells may be on the same or different multi-well plates, and in certain embodiments, the first population of cells and the untreated population of cells are present in a first multi-well plate. The method may further include the step of obtaining values for another untreated population of cells grown on a second multi-well plate, and identifying ranges of values for each of the cytological attributes that, together, distinguish the first population of contacted cells from the second population of contacted cells, the untreated population of cells grown on the first multi-well plate, and the second untreated population of cells. Further untreated populations of cells, grown on different multi-well plates or grown at different times (e.g., within at least a week, month or year earlier or later than the time at which the first population of cells was grown) may also be employed.

Figure 5:
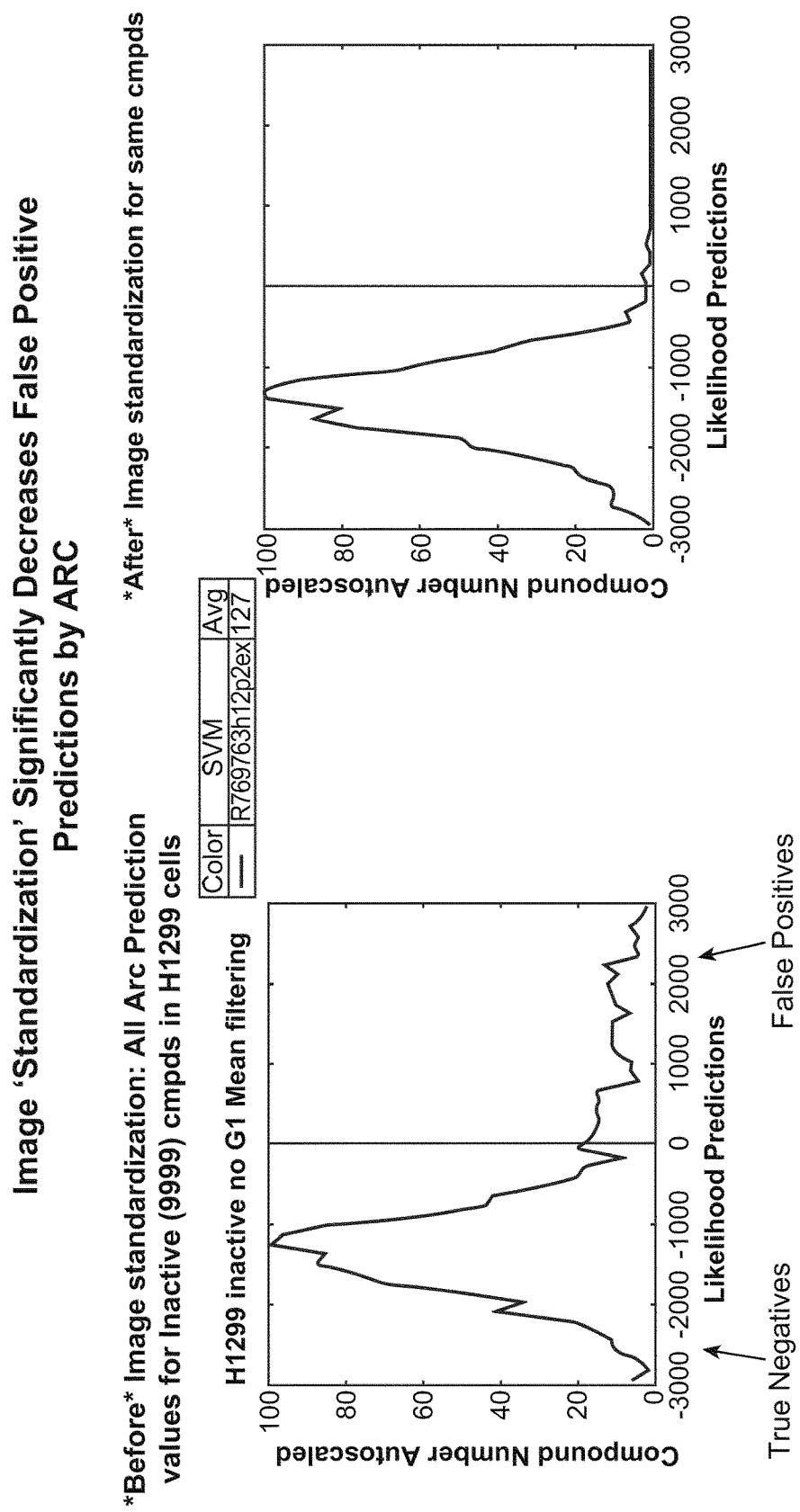
FIG. 5 shows that the image standardization method decreases false positive predictions.

Likewise, the method may also involve contacting a third population of cells with a third compound having a third known mode of action to provide a third population of contacted cells, obtaining values for the plurality of cytological attributes of the third population of contacted cells, and identifying ranges of values for each of the cytological attributes that, together, distinguish the first population of contacted cells from the second and third populations of contacted cells and the untreated population of cells. Further images of populations cells that have been exposed to other bioactive agents with different modes of action may also be employed. As with the untreated cells, these cells may be grown on different multi-well plates or grown at different times (e.g., within at least a week, month or year earlier or later than the time at which the first population of cells was grown). As illustrated in FIG. 5, the classifier becomes more robust as more untreated populations of cells and more populations of cells that have been exposed to bioactive agents having different modes of action are used to build the classifier. The classifier for each bioactive agent may be recalculated periodically using new data.

In general terms, the bioactive agents that are used to define a classifier are used at concentrations at which they produce a phenotype. For example, the bioactive agents may be employed at a concentration that is at or above their EC50.

Exemplary bioactive agents that can be employed in this method and their modes of action are shown in FIG. 16. Of particular interest are chemotherapeutic agents for the treatment of cancer, and anti-inflammatory agents. The agent may target a cell surface receptor (e.g., a GPCR or cell surface tyrosine kinase receptor), or a cytoplasmic protein, for example. In some embodiments, the bioactive agent may be an antisense RNA, or an inhibitory RNA molecule (which may be administered directly to the cell or indirectly to the cell using a vector encoding the RNA, for example).

Exemplary agents that can be employed in this method include:

(i) antiproliferative/antineoplastic drugs such as alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) anti-invasion agents (for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341), N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; J. Med. Chem., 2004, 47, 6658-6661), and bosutinib (SKI-606), and metalloproteinase inhibitors like marimastat, inhibitors of urokinase plasminogen activator receptor function or antibodies to Heparanase);

(iv) inhibitors of growth factor function: for example, such inhibitors include growth factor antibodies and growth factor receptor antibodies (for example the anti-erbB2 antibody trastuzumab [Herceptin™], the anti-EGFR antibody panitumumab, the anti-erbB1 antibody cetuximab [Erbitux, C225] and any growth factor or growth factor receptor antibodies disclosed by Stem et al. Critical reviews in oncology/haematology, 2005, Vol. 54, pp 11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI-774), and 6-acrylamido-N-(3-chloro-4-fluorophenyl)-7-(3-morpholinopropoxy)-quinazolin-4-amine (CI 1033), and erbB2 tyrosine kinase inhibitors such as lapatinib); inhibitors of the hepatocyte growth factor family; inhibitors of the insulin growth factor family; inhibitors of the platelet-derived growth factor family such as imatinib and/or nilotinib (AMN107); inhibitors of serine/threonine kinases (for example Ras/Raf signalling inhibitors such as farnesyl transferase inhibitors, for example sorafenib (BAY 43-9006), tipifarnib (R115777) and lonafarnib (SCH66336)), inhibitors of cell signalling through MEK and/or AKT kinases, c-kit inhibitors, abl kinase inhibitors, PI3 kinase inhibitors, Plt3 kinase inhibitors, CSF-1R kinase inhibitors, IGF receptor (insulin-like growth factor) kinase inhibitors; aurora kinase inhibitors (for example AZD1152, PH739358, VX-680, MLN8054, R763, MP235, MP529, VX-528 AND AX39459) and cyclin dependent kinase inhibitors such as CDK2 and/or CDK4 inhibitors;

(v) antiangiogenic agents such as those which inhibit the effects of vascular endothelial growth factor, for example the anti-vascular endothelial cell growth factor antibody bevacizumab (Avastin) and for example a VEGF receptor tyrosine kinase inhibitor such as vandetanib (ZD6474), vatalanib (PTK787), sunitinib (SU11248), axitinib (AG-013736), pazopanib (GW 786034) and 4-(4-fluoro-2-methylindol-5-yloxy)-6-methoxy-7-(3-pyrrolidin-1-ylpropoxy)-quinazoline (AZD2171; Example 240 within WO 00/47212), compounds such as those disclosed in International Patent Applications WO97/22596, WO 97/30035, WO 97/32856 and WO 98/13354 and compounds that work by other mechanisms (for example linomide, inhibitors of integrin αvβ3 function and angiostatin);

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) an endothelin receptor antagonist, for example zibotentan (ZD4054) or atrasentan;

(viii) antisense therapies, for example those which are directed to the targets listed above, such as ISIS 2503, an anti-ras antisense;

(ix) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy.

The bioactive agent used in the method may be an antitumor alkylating agent, antitumor antimetabolite, anti-tumor antibiotic, plant-derived antitumor agent, antitumor platinum complex, antitumor camptothecin derivative, anti-tumor tyrosine kinase inhibitor, monoclonal antibody, interferon, biological response modifier, hormonal anti-tumor agent, anti-tumor viral agent, angiogenesis inhibitor, differentiating agent, PI3K/mTOR/AKT inhibitor, cell cycle inhibitor, apoptosis inhibitor, hsp 90 inhibitor, tubulin inhibitor, DNA repair inhibitor, anti-angiogenic agent, receptor tyrosine kinase inhibitor, topoisomerase inhibitor, taxane, agent targeting Her-2, hormone antagonist, agent targeting a growth factor receptor, or a pharmaceutically acceptable salt thereof. In some embodiments, the anti-tumor agent is citabine, capecitabine, valopicitabine or gemcitabine. In some embodiments, the agent is selected from the group consisting of Avastin, Sutent, Nexavar, Recentin, ABT-869, Axitinib, Irinotecan, topotecan, paclitaxel, docetaxel, lapatinib, Herceptin, lapatinib, tamoxifen, a steroidal aromatase inhibitor, a non-steroidal aromatase inhibitor, Fulvestrant, an inhibitor of epidermal growth factor receptor (EGFR), Cetuximab, Panitumimab, an inhibitor of insulin-like growth factor 1 receptor (IGF1R), and CP-751871.

In one embodiment, the performance of a classifier may be evaluated by contacting further populations of cells with the test compound (i.e., the same compound as contacted with the first population of cells), obtaining values for the cytological attributes of individual cells in those populations of cells, and determining if the values correctly classify the individual cells. The results from these assays can be summed to provide a performance characteristic for that new classifier that indicates the true positive/true negative rate of the classifier. As would be expected, some cells in a population of cells exposed to an agent having a known mode of action retain a "wild-type" appearance and may resemble controls that are not contacted with the agent. This performance characteristic, among other things, accommodates for variation in the phenotype in individual cells in a population. The method provides a metric of classifier performance, which, as described below, may be employed to calculate a likelihood score using, for example, Bayesian theory.

Screening Method

As noted above, a screening method is provided in which a population of cells is contacted with a test agent, values for cytological attributes are obtained, and the values are compared to a classifier in order to determine if the cells can be classified by the classifier. The comparison provides a score of the likelihood that the agent produces the same phenotype as that used to produce the classifier. The method may further comprise identifying a test compound having a desired mode of action.

In certain embodiments, the method involves: contacting a population of test cells with a test compound to provide contacted test cells; obtaining values for a plurality of cytological attributes of the contacted test cells; and scoring the contacted test cells using the values to provide a likelihood score for at least one of a plurality of classifiers, where the plurality of classifiers are defined using values for the cytological attributes obtained from cells that have been contacted with compounds of known mode of action. A plurality of assays may be run in parallel with different agent concentrations to obtain a differential response to the various concentrations. The concentrations may be chosen to encompass an agent's predicted EC50. In particular embodiments, the concentration used in the assay that is immediately above an agent's EC50 (i.e., the agent's "EC50+1") may be used in the method.

In particular embodiments, the values may be obtained by capturing an image of the contacted test cells and analyzing the image to provide the values. The image may be captured using an automated microscope and the analysis may be done by a computer operably linked to the automated microscope.

The scoring may be done by comparing values obtained from the individual cells in the population to a classifier; determining whether the individual cells are classified or are not classified by the classifier, thereby providing a binomial output indicating whether the cell is or is not classified; and calculating the likelihood score using the number of individual cells in the population that are classified by the classifier and the number of individual cells in the population that that are not classified by the classifier. In certain embodiments and as illustrated in FIG. 9, the scoring employs a Bayesian theory that uses a metric of the performance of the classifier as an input. As explained above, this metric can be experimentally determined by contacting test cells with the same compound as that used to contact the cells to produce the classifier, and then determining whether the test cells are classified by the classifier. More robust classifiers correctly classify test agents more than less robust classifiers. In certain cases, the likelihood score is calculated by inputting the binomial output of the comparison (which indicates the number of individual cells in the population that are classified by the classifier and the number of individual cells in the population that that are not classified by the classifier), and the performance score of the classifier.

In some embodiments, a population of cells is contacted with a test agent, and the values for the population of cells are compared to at least one classifier (e.g., one classifier, two or more classifiers, or all classifiers) of a plurality of different classifiers, where each classifier is determined using an agent having a known mode of action. For example, the values may be compared to at least two, at least 5, at least 10, at least 20, up to 50 or 100 or more classifiers, where each of the classifiers is determined using a different agent having a known mode of action.

Figure 17:
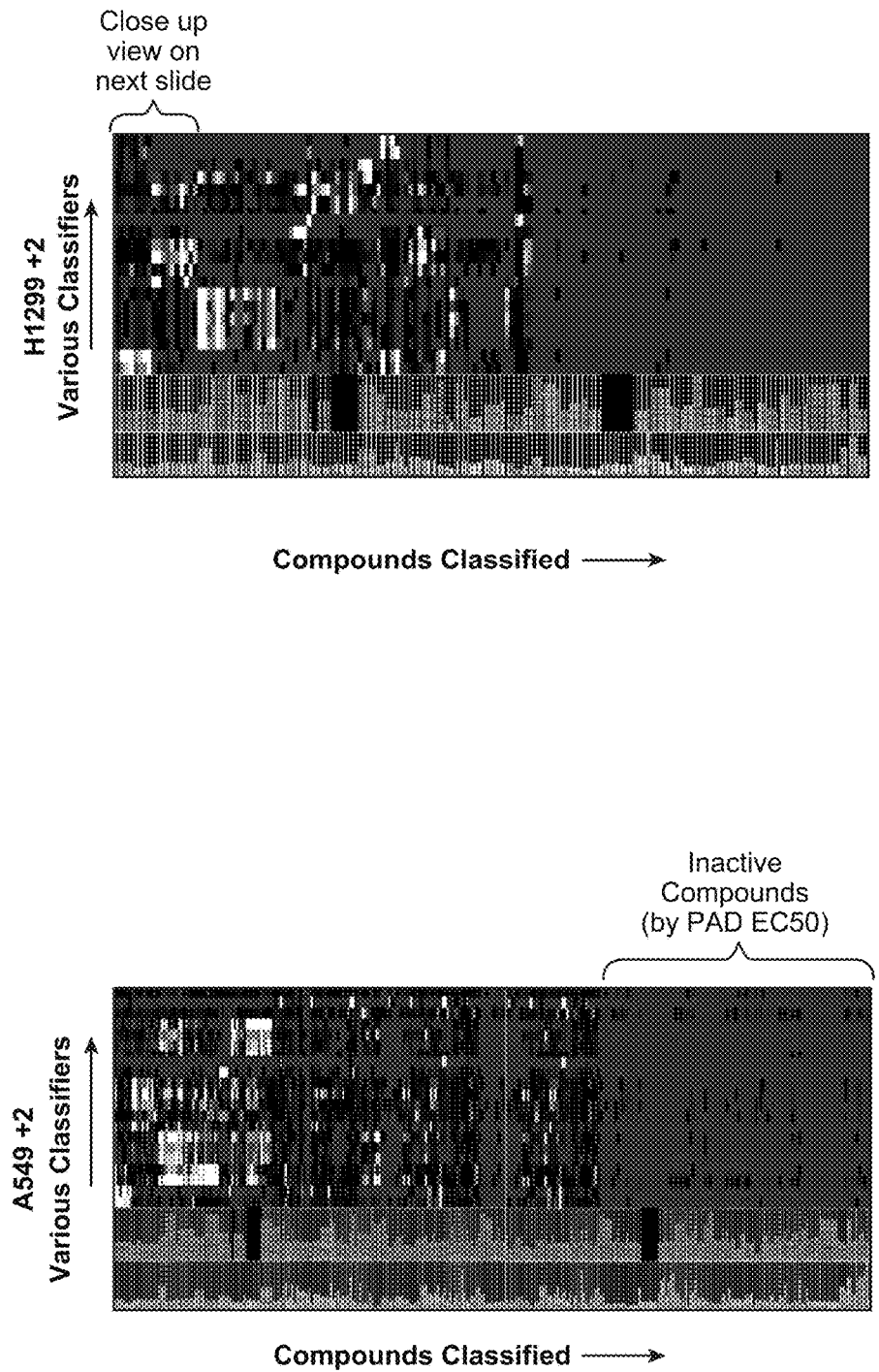
FIG. 17 shows heatmaps that reveal phenotypic patterns.
Figure 18:
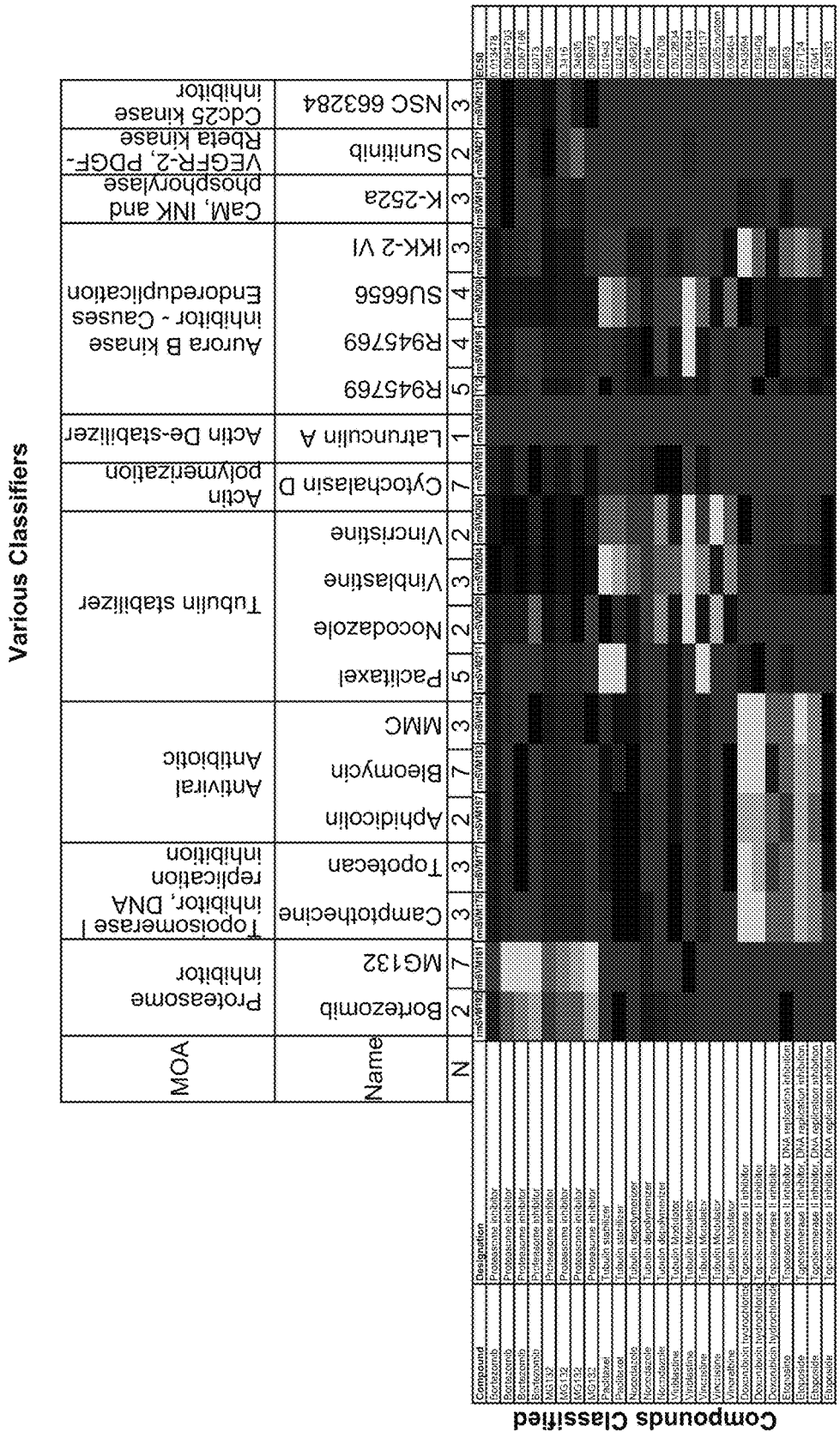
FIG. 18 shows a close-up of a portion of the heatmap shown in FIG. 17.

In particular embodiments and as illustrated in FIGS. 17 and 18, the method may be employed to produce, for each test compound, a likelihood score for each of a plurality of different classifiers. The profile of likelihood scores may be cross-compared with one another to identify agents that have similar likelihood score profiles. Such a hierarchical cluster analysis method may be adapted from the methods generally described in Eisen (*Cluster analysis and display of genome-wide expression patterns* Proc. Natl. Acad. Sci. 1998 95: 14863-14868) and Ling (*A computer generated aid for cluster analysis*. Communications of the ACM 1973 16: 355-361), for example. In one embodiment, the cluster analysis may be used to generate a so called "heat map", i.e., a two dimensional graphical representation of data where the likelihood scores are represented by different colors and/or different intensities, where the compounds are listed in one dimension and classifiers in the other. A tree map may also be generated. Using this method, test agents may be clustered by their mode of action, and test agents having a similar likelihood score profile to an agent with a known mode of action may be identified.

In particular embodiments, such an analysis may be employed to identify compounds with other modes of action, i.e., modes of action that are different to those represented by the classifiers. In these embodiments, certain test compounds may provide a new pattern of scores for a plurality of classifiers, thereby indicating that the test compounds have a third mode of action. For instance, a test compound may be strongly or intermediately positive for a combination of two or more classifiers, in which case the test compound may have a mode of action that is different to those used to define the classifiers. Thus, compounds having a mode of action that is different to those used to define the classifiers may still be identified. In particular embodiments, the new mode of action may be identified only after a number of different test compounds have been assayed and a pattern that is consistently different to the patterns produced by the compounds of known mode of action has been identified. In these embodiments, a test compound with a different pattern may be tested to further define the mode of action of that compound.

Classifier performance may also be evaluated using other statistical means, e.g., using precision (which is a measure of exactness, i.e., how frequently the method produces false positives and false negatives) and recall (which is a measure of completeness, i.e., how well the method identifies desired compounds) metrics, as illustrated in FIG. 10. As illustrated in FIG. 10, in this method, precision may be defined as the number of items correctly labeled as belonging to the positive class divided by the total number of elements belonging to the positive class, whereas recall may be defined as the number of true positives divided by the total number of elements that actually belong to the positive class. Methods for calculating precision and recall are described in Makhoul et al (Performance measures for information extraction. In: Proceedings of DARPA Broadcast News Workshop, Herndon, Va., February 1999).

In certain embodiments, the test agent has an unknown mode of action. In particular embodiments, the test agent may be a bioactive agent or a derivative thereof, identified using a different screen, where the term "agent" as used herein describes any molecule, e.g. protein or non-protein organic or inorganic compound. Test agents encompass numerous chemical classes, e.g., synthetic, semi-synthetic, or naturally-occurring inorganic or organic molecules. Candidate agents include those found in large libraries of synthetic or natural compounds. For example, synthetic compound libraries are commercially available from Maybridge Chemical Co. (Trevillet, Cornwall, UK), ComGenex (South San Francisco, Calif.), and MicroSource (New Milford, Conn.). Alternatively, libraries of natural compounds in the form of bacterial, fungal, plant and animal extracts are available from Pan Labs (Bothell, Wash.) or are readily producible.

Candidate agents may be small organic or inorganic compounds having a molecular weight of more than 50 and less than about 2,500 Da. Candidate agents may comprise functional groups necessary for structural interaction with proteins, particularly hydrogen bonding, and may include at least an amine, carbonyl, hydroxyl or carboxyl group, and may contain at least two of the functional chemical groups. The candidate agents may comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. New potential therapeutic agents may also be created using methods such as rational drug design or computer modeling.

Screening may be directed to known pharmacologically active compounds and chemical analogs thereof, or to new agents with unknown properties such as those created through rational drug design.

Agents that modulate a phenotype may decrease the phenotype by at least 10%, at least 20%, at least 30%, at least 40%, at least 50%, at least 60%, at least 70%, at least 80%, or at least 90%, or more, relative to a control that has not been exposed to the agent.

Agents of interest may be subjected to directed or random and/or directed chemical modifications, such as acylation, alkylation, esterification, amidification, etc. to produce structural analogs. Such structural analogs include those that increase bioavailability, and/or reduced cytotoxicity. Those skilled in the art can readily envision and generate a wide variety of structural analogs, and test them for desired properties such as increased bioavailability and/or reduced cytotoxicity, etc.

The cultured cell employed in the assay may be any cell, including immortalized cells and inflammatory system cells which can be screened to identify anti-cancer and anti-inflammatory agents, respectively. Cultured cells from any animal, e.g., cultured mammalian cells, may be employed, including but not limited to: monkey kidney cells (COS cells), monkey kidney CV1 cells transformed by SV40 (COS-7, ATCC CRL 165 1); human embryonic kidney cells (HEK-293, Graham et al. J. Gen Virol. 36:59 (1977)); baby hamster kidney cells (BHK, ATCC CCL 10); chinese hamster ovary-cells (CHO, Urlaub and Chasin, Proc. Natl. Acad. Sci. (USA) 77:4216, (1980); mouse sertoli cells (TM4, Mather, Biol. Reprod. 23:243-251 (1980)); monkey kidney cells (CV1 ATCC CCL 70); african green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (hep G2, HB 8065); mouse mammary tumor (MMT 060562, ATCC CCL 51); TR1 cells (Mather et al., Annals N.Y. Acad. Sci 383:44-68 (1982)); NIH/3T3 cells (ATCC CRL-1658); and mouse L cells (ATCC CCL-1). Additional cell lines will become apparent to those of ordinary skill in the art. A wide variety of cell lines are available from the American Type Culture Collection, 10801 University Boulevard, Manassas, Va. 20110-2209. In particular embodiments, the cultured cell may be a cultured myocyte, e.g., a cultured cell of skeletal muscle, smooth muscle, or cardiac muscle origin. Methods for culturing such cells are known.

In particular embodiments, the method may be used to identify an agent that does not produce "side-effects" e.g., undesirable phenotypic changes to a cell. In certain cases, a test agent having a desired mode of action has a profile of likelihood scores that is similar to those of an agent of known mode of action. Any agent identified by the above-described method may be tested in a further in vitro assay or using an animal model prior to a clinical evaluation.

Microscopy System

Consistent with the above, a microscopy system is also provided. This system comprises: a device for capturing an image of a population of cells (which may contain a digital camera (e.g., a CMOS camera), an appropriate light source (e.g., a lasers, etc.) and a optical system that may include a beam splitter, a polarizer, a prism, a filter and lenses for transporting light from the light source to the population of cells and for transporting light from the cells to a detector); and a computer, operably linked to the device via, e.g., a cable or wireless connection, that contains programming for: i. analyzing an image of cells to provide values for a plurality of cytological attributes of the cells in the image; and ii. scoring the cells using the values to provide a likelihood score for at least one of a plurality of classifiers, where, as noted above, the plurality of classifiers are defined using values for the cytological attributes obtained from cells that have been contacted with compounds of known mode of action. The device of the microscopy system may be an automated microscope.

In one embodiment, a physical memory of the computer contain a physical computer-readable medium containing instructions (i.e. "programming") for performing the method described above. The programming can be provided in a physical storage or transmission medium. A computer receiving the instructions can then execute the algorithm and/or process data obtained from the subject method. Examples of storage media that are computer-readable include floppy disks, magnetic tape, DVD, CD-ROM, a hard disk drive, a ROM or integrated circuit, a magneto-optical disk, or a computer readable card such as a PCMCIA card and the like, whether or not such devices are internal or external to the computer. A file containing information can be "stored" on computer readable medium, where "storing" means recording information such that it is accessible and retrievable at a later date by a computer on a local or remote network.

In one embodiment, data from the microscope is collected, and programming containing the classifier is executed. The method described above can be executed (automatically or manually) each time a sample is run.

EXAMPLES

The following examples are provided in order to demonstrate and further illustrate certain embodiments and aspects of the present invention and are not to be construed as limiting the scope thereof.

Materials

Active compounds are suspended in DMSO to a concentration of 10 mM from powder.

Controls: DMSO (Sigma-Aldrich (St. Louis, Mo.), D2650), Taxol (T7402) and Etoposide (E1383) (Sigma-Aldrich (St. Louis, Mo.)

Cell Lines: Tumor cell lines were obtained from ATCC and cultured using the recommended media. Cell splitting was done with calcium and magnesium-free Phosphate Buffered Saline (PBS) and Trypsin-EDTA (25-052-CI) obtained from Mediatech.

| Cell Lines | Tissue Origin | Media | PAD | Provider | Location of Raw Data (Pages)* |
|---|---|---|---|---|---|
| A549 | Lung | F12K + FCS(10%) + PS | 1.9 | ATCC (CCL-185) | 1 |
| H1299 | Lung | RPMI1640 + FCS(10%) + PS | 1.9 | ATCC (CRL-5803) | 2 |

Equipment: Cells were imaged on a MDS IX5000 fluorescent microscope equipped with a 10×S Fluor objective, a Xenon light source, Chroma Filters for Dapi and Texas Red and a CCD camera. Hardware components were connected to a PC using Win2000 operating system and controlled with MetaX software (MDS Molecular Devices, Sunnyvale, Calif. USA). Images were captured and analyzed in 16-bit format using segmentation and morphological routines contained in the CellProfiler image analysis software (Broad Institute Boston, Mass. USA). Identified nuclei were counted and pixel data for each cell along with experimental conditions were stored in a MySQL 5.0 database. Subsequent analysis of experimental results and graph creation including $EC_{50}$ curve fitting was performed with MatLab R2007b (MathWorks Inc. Natick, Mass. USA).

Methods

| | |
|---|---|
| NCI: National Cancer Institute | aa: Amino Acids |
| ATCC: American Tissue Culture Collection | Glc: Glucose |
| PAD: Plating density in 96-well plates (×1000 cells/well) | Gln: Glutamine |
| PS: Penicillin/Streptomycin | BSA: Bovine Serum Albumin |
| FBS: Fetal Bovine Serum | |

Experiments were performed in RPMI 1640 modified media with L-Glutamine (Mediatech 10-040-CM) and 5% FBS and Pen/Strep. Cells were plated using a Labsystems Multidrop 384 at an empirically determined density in ViewPlate96 96-well plates from Packard and allowed to grow for 24 hours prior to the addition of compounds in duplicate replicates. The compound dilutions for the 6-point were performed on a Beckman FX. Following incubation with the compound for 48 hours, cells were fixed with 2.0% paraformaldehyde (Alf Aesar 16% solution) in PBS (Ca++/Mg++-free) for 1 hour, washed with PBS 2×, stained overnight with 1:1000 phalloidin-Alexa 568 from Invitrogen (A12380) then washed 1× and stained for 60 minutes with a 6 ng/mL solution of 4'6-diamidino-2-pheylindole, dihydrochloride (DAPI) in PBS from Invitrogen (D-1306), and washed with PBS. Fixing, washing and staining were performed using a Bio-Tek Elx405 plate washer integrated with a Beckman FX.

Nine images per well were taken in an adjacent grid pattern in each well of the 96 well plates of treated tumor cells. Normally all conditions were done in duplicate on each plate. Dose responses were done at six concentrations per curve (each concentration in duplicate) in 3-fold serial.

Results for the nine images per well were summed for each well and then averaged across duplicates. $EC_{50}$s were generated by fitting the cell counts to a variable slope four parameter sigmoidal dose response curve using non-linear least squares method with the Trust-Region algorithm. Error bars on dose response points reflect standard deviations. Data was fit using five different sets of parameters forcing the top or the bottom to negative or positive (or zero) controls (Taxol 20 nM, Etoposide 5 uM) included on each plate. The different parameter sets were bottom to zero, bottom to the most potent of either of the positive controls, bottom to the positive control and the top to the negative control, bottom to zero and the top to the negative control and one curve was fit by letting the top and bottom float. All fits allowed the slope to float. The best fit for each compound was assessed by manual inspection after taking into account the quality of the fit and the biological relevance of the fit result. Inactive compounds were designated 9999 for $EC_{50}$.

Cell cycle results were determined by manual inspection of the DNA content 1D frequency histograms output by the PAD analysis platform. DNA content plots were smoothed using the Lowess method. Generally results were coded as G1, G2, G1/G2 arrest, absent or as 'Cannot determine'. Apoptosis was also assessed by manual inspection of sample images for fragmented nuclei. The concentration at which significant fragmented nuclei were first observed is the value recorded for Apoptosis. Observations were noted in a comments section for each compound.

Z' results were calculated per plate using the DMSO negative control and a high dose of the positive controls Taxol and Etoposide.

Assay Biology, Microscopy and Image Analysis: The tumor cell line H1299 from ATCC was cultured in media with 10% Fetal Bovine Serum and without Pen-Strep. Cells were plated using a Multidrop on 96-well Corning plates at a density of 18K per ml and allowed to grow for 24 hours prior to the addition of compounds. Cell plating and further experiments were performed in RPMI with 5% FBS and 1% P/S. Compound dilutions were performed in DMSO on a Beckman FX equipped with a Span-8 pod. Following 48 hours incubation, cells were fixed and stained for 1 hour with 2% PAF, then washed with a Elx405 plate washer, incubated for 18 hrs with Alexa-568 Phalloidin at 1:1000 and washed again and stained for 1 hr with a 7 ng/mL solution of DAPI. The assay was performed weekly. Five compounds per plate were dosed in 6 point at 3-fold serial dilution in duplicate. Each plate contained DMSO negative controls and the positive controls Taxol and Etoposide at a single concentration. Five fields per well were taken of both DAPI and Actin at 35 ms and 150 ms, respectively, with a MDS IX5000A using a 20× Plan Apo objective. Images were exported as tiffs and analyzed using CellProfiler (CP). Nuclear regions were found in the DAPI using Otsu's method and cytoplasmic regions in Actin with the CP Propagation algorithm. All intensity, position, area, shape and texture (at 3 pixel distance) feature measurements available in CP were collected into a MySQL database. Correlation information was not included. 70 features each for color gave 140 features per cell. As compounds were tested, dose response curves were inspected to assure proper EC50 determination. Images were inspected and a morphological category or QC comments were noted if appropriate.

Example 1

Training Set Generation Strategy

Figure 6:
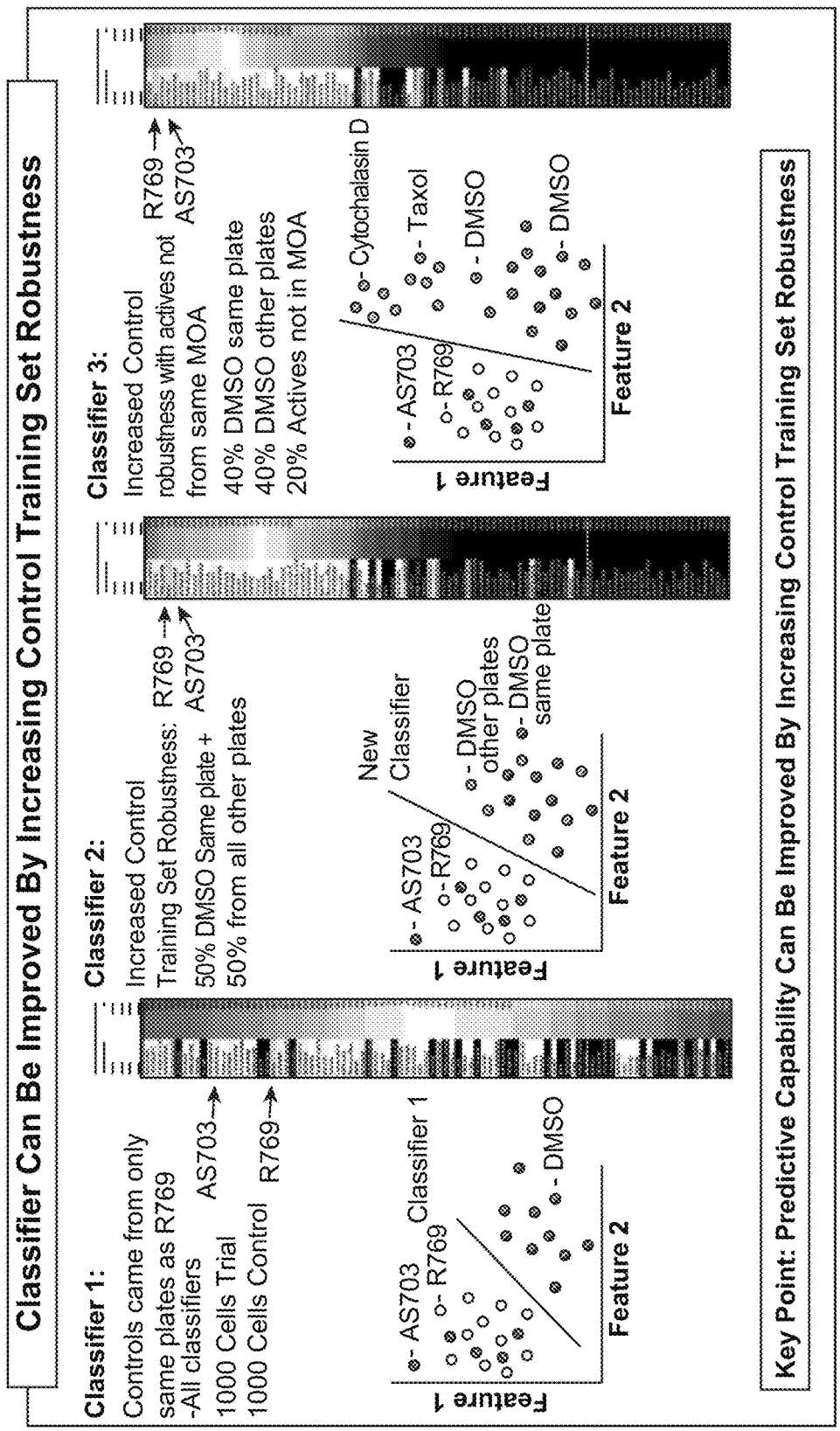
FIG. 6 shows that classifiers can be made more robust by increasing the number of control training sets.
Figure 7:
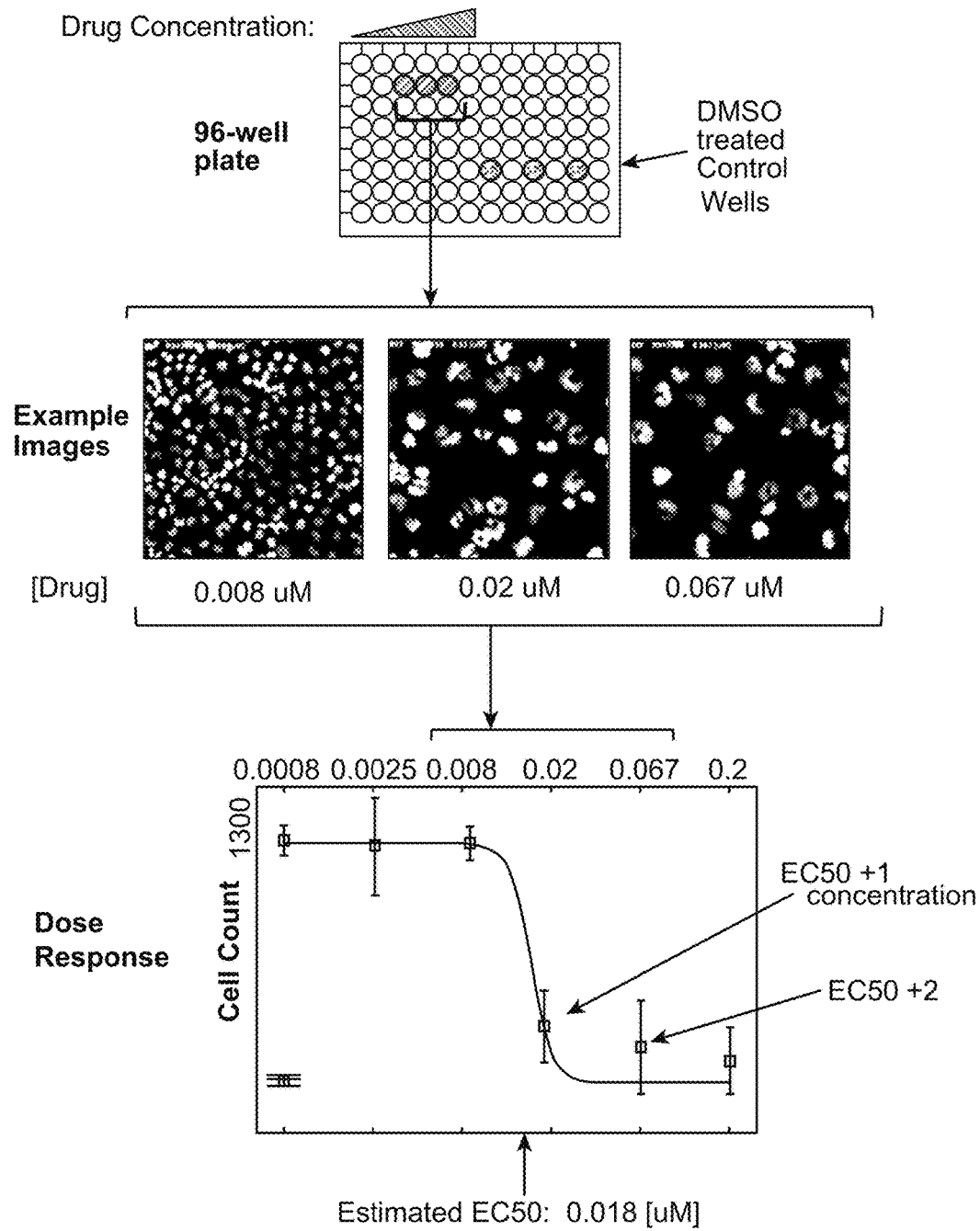
FIG. 7 schematically illustrates a typical dose calculation.

Training sets were drawn from treatment wells at concentrations in relation to the EC50 for that compound. FIG. 7 shows images from three wells of a six-point dose response with one well below the estimated EC50 and two above. One treatment training set is drawn from the first concentration above the EC50 and a different one from the second step. Classifiers generated to these training sets were applied to their respective concentrations. This strategy allowed for comparison of compounds with different EC50 response ranges to be compared. Control (DMSO) treated cells were drawn randomly from negative control wells contained in each plate. Training sets were generally 1000 cells, if available. As illustrated by FIG. 6, classifiers were made more robust by adding training sets of DMSO controls from other plates and compounds having a different mode of action.

Example 2

Classifier Generation Strategy

FIG. 8 shows how classifiers are trained and how new data is classified and analyzed to provide a prediction value. After standardizing feature values for all cells in a training set and mapping to feature space classifiers were trained to differentiate between DMSO treated wells and wells exposed to one of the MOA control compounds using the 140 features measured for each cell. These new classifiers were then used to classify results from a 100 compound test set of newly assayed compounds. Due to the binary classification nature of svm algorithms all the cells in every well were classified as either like control (DMSO) or trial (compound) yielding a binomial distribution. As classifiers were trained performance characteristics were obtained. The process most likely responsible for a well's labeled results could be found by taking the ratio of the probability that the process is trial given the observed results to the probability the process is control. This is the likelihood ratio that can be written in the form of Bayes Theorem. Given a classifer's performance characteristics and number of cells classified as either trial or control, the binomial coefficient was used to find the likelihood ratio. This value is the prediction value reported in the figures which typically ranged from −2000 to +500, across many classifiers, cell lines and a few thousand compounds, with negative values predicting similarity to control and positive values meaning similarity to trial.

Classifiers were generated against the 140 features for each cell. Ranges for features collected were standardized using the mean and standard deviation of each feature. Parameters were selected by examining the 'grid' of possible parameter values for a SVM using a radial kernel. C and gamma were varied between 0.01 and 10, and 0.001 and 1, respectively. Five steps were chosen in each direction to give 25 possible parameter pairs. For each parameter pair 3-fold cross-validation accuracy was calculated. SVM were trained using the full 'control' and 'experimental' training sets and then tested on the standardized 'control' and 'experimental' test sets, and basic quality control measures including the per-well false positive and negative rate were calculated. The composition of control training sets was varied to increase accuracy as described below.

Training sets were created from treated wells spanning ~1000 96-well plates screened over a year and a half. Compounds with known mechanisms of action (MOA) were identified and used to investigate the ability of classifiers to generalize beyond the specific treatment for a given training. These groups included inhibitors to AuroraB, the 26S proteosome, Tubulin, Actin, Topoisomerase I, and antibiotic DNA synthesis. Classifiers created for these groups used training sets containing 40% each DMSO from the same plate as the trial and 40% from any other plate, in addition to 20% from wells treated with compounds that were not of similar MOA. For example, R769 classifier control training sets contained cells treated with MG132, Taxol, Latrunculin A, and Camptothecin (and other similar compounds), but not any "AS" compounds, which had known AuroraB activity. After creating these classifiers, 100 compounds including the above mentioned, along with known inactive compounds and other controls, were retested in the PAD_48 hr assay. Classifier results shown are for the retested 100 compounds.

Example 3

Well Classification Strategy

One goal is to look at the cells from a given well and infer which process generated the cells. A binary classifier is the tool used at the cell level to say whether the cell was more likely to have been generated via trial or control. As classifiers were trained performance characteristics were obtained. Given these characteristics and the fraction of a given well labeled as trial or control by the classifier the process most likely responsible for a well's labeled results could be found by taking the ratio of:

P(process=X or 'trial'|data)—the probability that the process is trial given the observed results to:

P(process=Y or 'control'|data). This is the likelihood ratio.

The second term p (process=X)/p (process=Y) is the prior odds and is ignored under the assumption that either possibility is equally likely. Given a classifer's performance characteristics and number of cells classified as either trial or control, the binomial coefficient was used to find the likelihood ratio.

a and b are the probability of given classifier labeling a cell trial or control, respectively, and x and y are the number of cells classified trial or control. To avoid issues related to dividing very small numbers logarithm were used to calculate the likelihood for each model, and the difference between the two logarithms is reported. This value is the prediction value reported in the figures. Prediction values typically ranged from −2000 to +500, across many classifiers, cell lines and a few thousand compounds, with negative values predicting similarity to control and positive values meaning similarity to trial. This strategy is illustrated in FIG. 9.

svm classifiers are made to the moa control set of compounds. The number of experiments (essentially plates) the training set examples were drawn from is N. The classifier validation statistics are listed (True Pos, etc.) and the precision and recall of each svm against a test set of 100 compounds is listed as well. This is done for both the +1 set of svm's and the +2 set.

Example 3

Data Sets

The assay was performed weekly with all plates plated with cell, dosed, fixed and stained as a group. Compounds were dosed 5 to a 96 well plate in 6-point dose response in duplicate for each 96 well plate. On each plate a negative control of DMSO was dosed at the same percentage of concentration as compound dosing and positive controls Taxol and Etoposide were dosed at a single concentration. These controls were used to calculate Z prime factors for each plate and to assess the staining intensity from the cell cycle plots.

Digital images of DAPI stained nuclei were captured and segmented to locate nuclei and measure features such as intensity, area, shape and texture for each nuclei. We used CellProfiler to segment images and quantify features. As compounds were tested sample images from each concentration of the dose responses were visually inspected and a morphological category was assigned if appropriate. Dose response curves were inspected to assure proper EC50 determination and quality control assessments such as incorrect concentration range of dosing were annotated. Individual cell data, experimental properties and manual inspection results were stored in a custom built software system that allowed us to retrieve individual cell data by experimental properties such as compound name, concentration, and cell line and to filter out data from experiments of insufficient quality.

Figure 11:
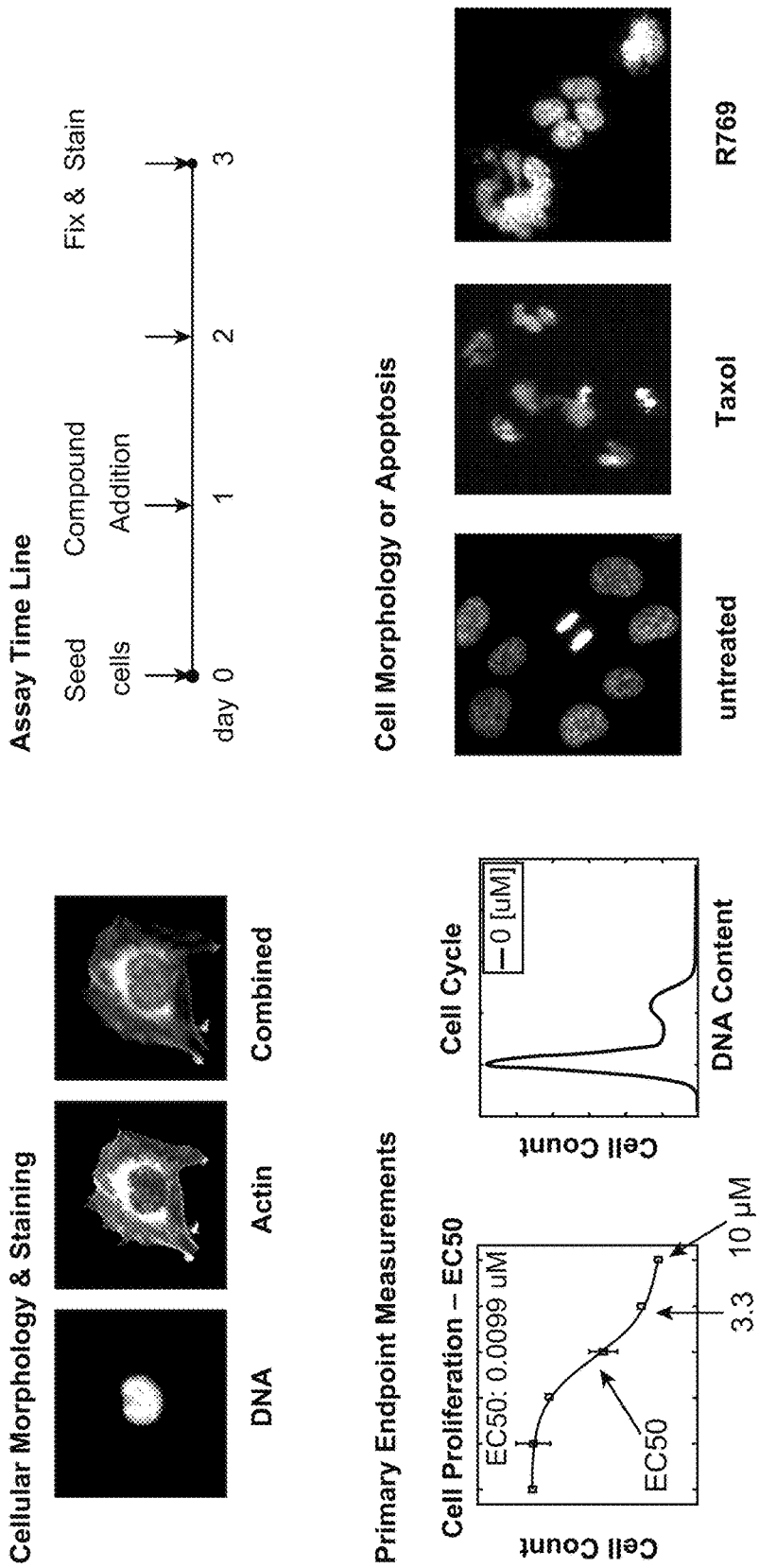
FIG. 11 illustrates an exemplary assay.
Figure 12:
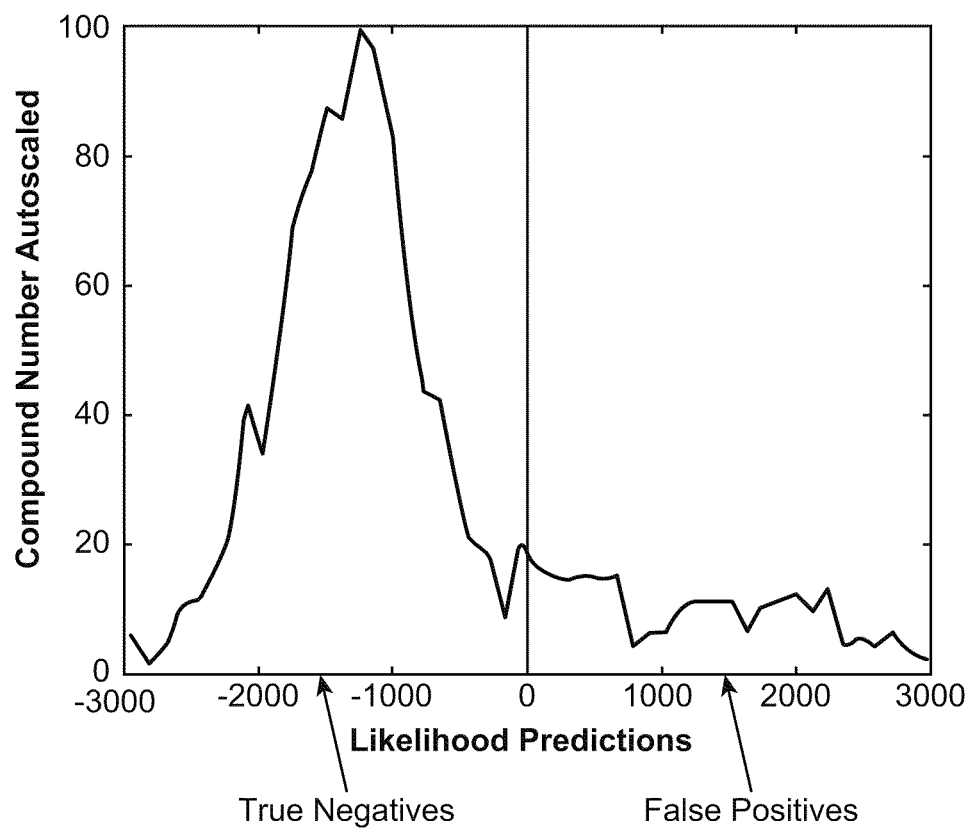
FIG. 12 is a graph of exemplary results.

FIG. 11 illustrates exemplary results from a proliferation-apoptosis-DNA content (PAD) assay, and FIG. 12 provides a graph of results obtained for inactive compounds screened by the subject method. Likelihood scores for true negatives and false positives are indicated.

Figure 14:
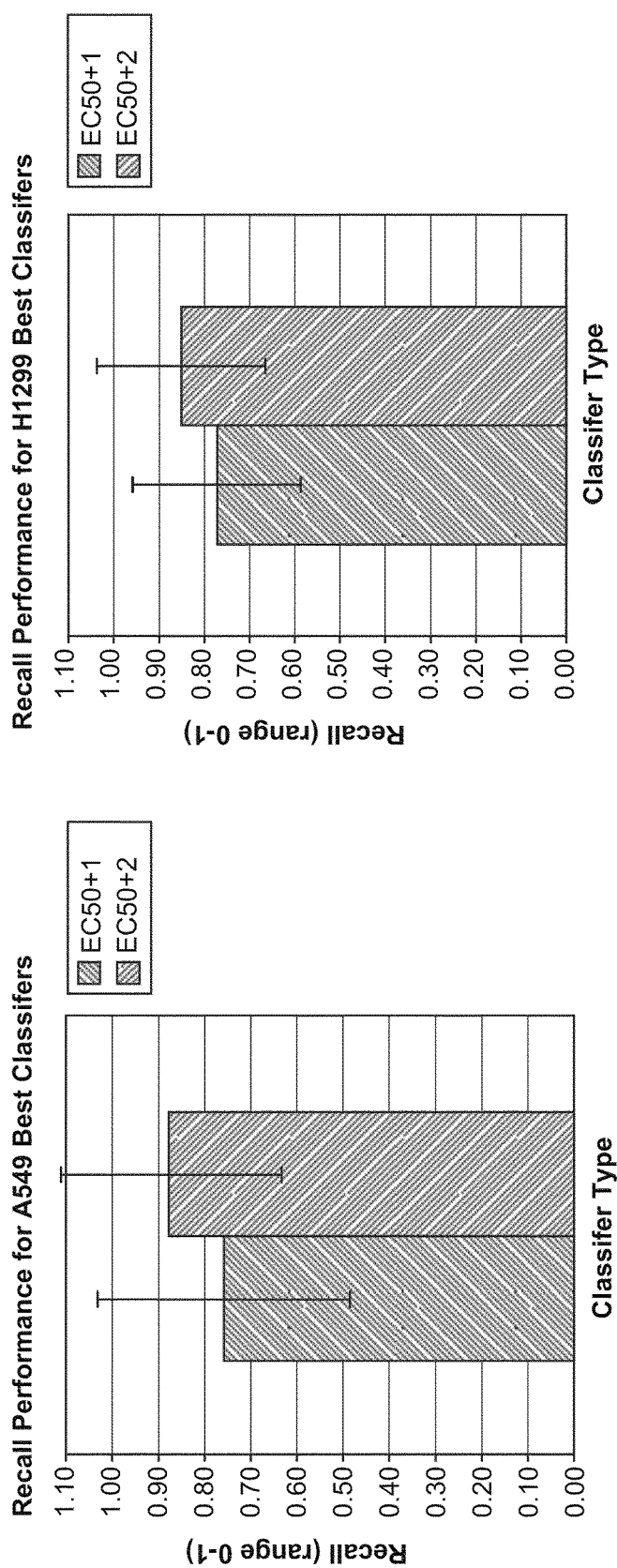
FIG. 14 shows graphs illustrating the average recall performance of some classifiers.
Figure 15:
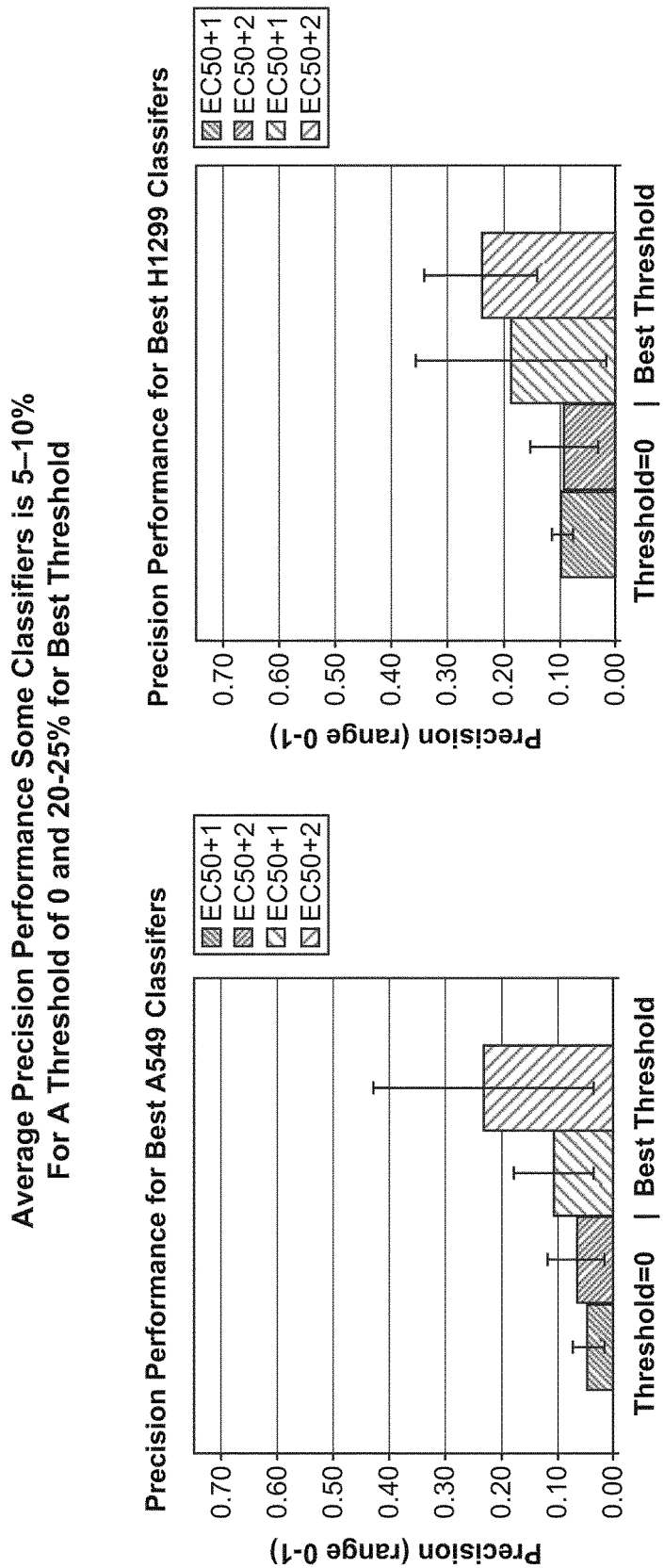
FIG. 15 shows graphs illustrating the average performance of some classifiers.

FIG. 13 is a table showing recall and precision results for selected classifiers. A threshold may be chosen for both the recall and precision in order to increase or decrease classifier robustness. FIG. 14 shows graphs illustrating the average recall performance of some classifiers, whereas FIG. 15 shows graphs illustrating the average precision performance of some classifiers.

Example 4

Image Standardization

Figure 2:
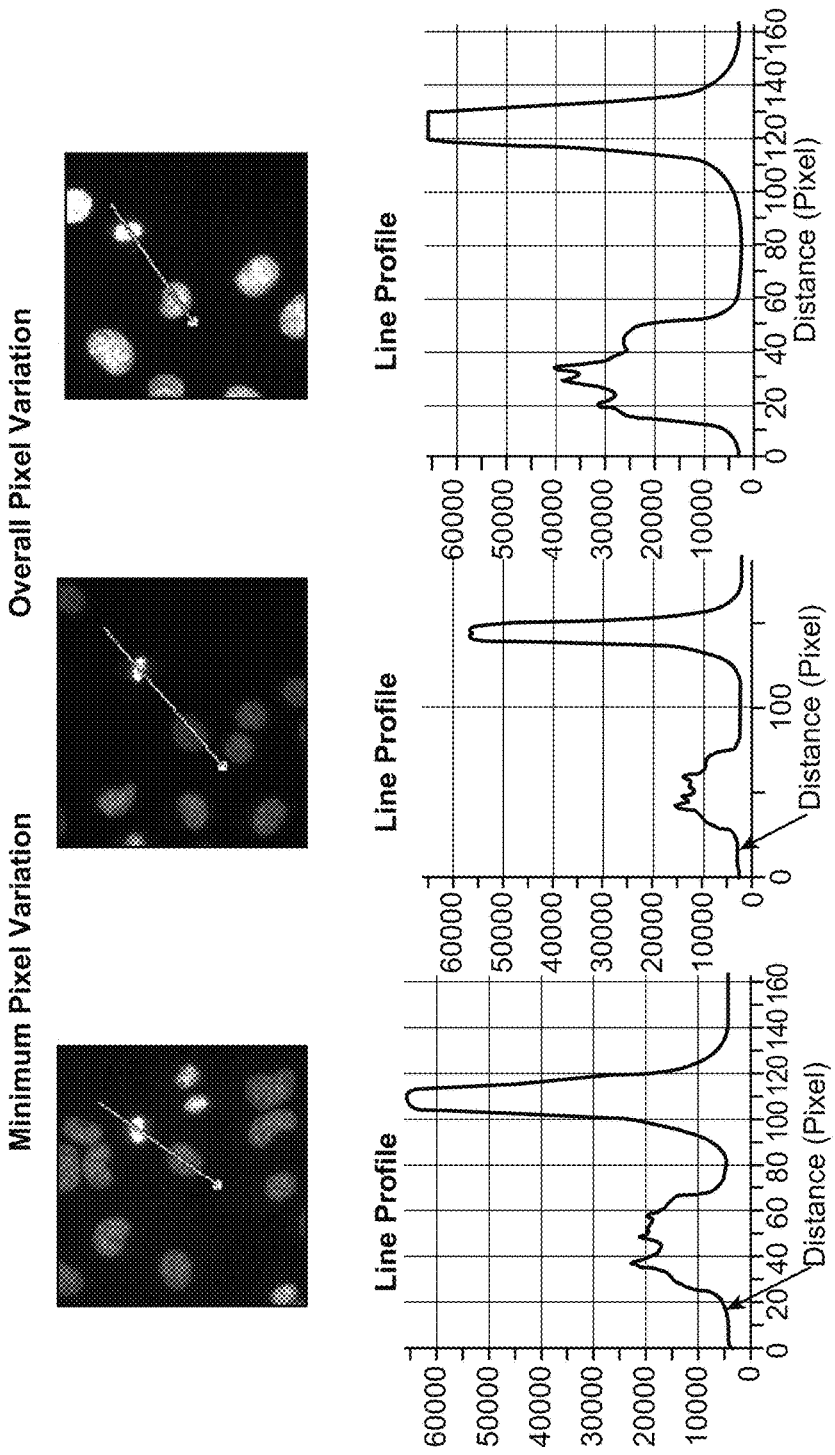
FIG. 2 shows that staining intensity is a major source of assay variation.

By keeping the assay parameters as consistent as possible it was determined that the primary sources of variation in the assay was the cell density and the cellular staining intensity (see. FIG. 2). This assay was performed in bulk each week thus assay intensity and cell density was normally very similar within each week's assay, but potentially different between weeks.

Fluctuations in the rate of cell growth over multiple passages and the individual plating the cells contributed to variations in cell density. Cell passage values were eventually confined to greater than 5 but less than 25. Other sources of variation in cell density were found to be difficult to control for but it has been determined that as long as the cell density is a above a fairly low minimum value the quality of the EC50 determination and ability to apply pattern recognition techniques is not effected by cell density differences.

A number of factors including instrument lamp intensity and length of staining contributed to changes in staining intensity. To compensate for this fluctuation images were standardized within each plate to control wells contained in each plate. This technique yielded significant improvements in classifier discrimination.

Images were standardized within each plate by first finding the median foreground intensity of the DMSO negative control. Then, for each treatment image, the median background of that image was subtracted and the result was divided by the control median foreground. Then each image was modified according to this formula: image+Offset/(Multiple*(1−Offset)='standardized image', where 'Offset' raises the image above zero and 'Multiple' is the number of times a treatment could reasonably be expected to be above the DMSO control. This method is illustrated in FIG. 3, and FIG. 4, with exemplary results shown in FIG. 2 and FIG. 5.

What is claimed is:

1. A screening method comprising:
   a) contacting a population of test cells with a test compound to provide contacted test cells;
   b) obtaining values for a plurality of cytological attributes of said contacted test cells;
   c) determining whether the phenotype of the test cells matches the phenotype of cells that have been treated with a compound having known mode of action, wherein the determining is done by:
      (i) obtaining a set of classifiers for a plurality of compounds of known mode of action, wherein the classifiers are defined using values for said cytological attributes obtained from cells that have been contacted with compounds of known mode of action; and
      (ii) calculating a likelihood score indicating the likelihood that the values obtained for the contacted cells match a classifier of the set of classifiers,
      wherein an increased likelihood score increases the confidence that the phenotype of the test cells matches the phenotype of cells that have been treated with a compound having known mode of action, and
   d) identifying the test compound as having a desired mode of action, wherein said test compound has a profile of likelihood scores that is similar to that of a compound of known mode of action.

2. The method of claim 1, wherein said determining is done by:
   comparing values obtained from the individual cells in said population of contacted test cells to a classifier;
   determining whether the individual cells are classified or are not classified by said classifier; and
   calculating said likelihood score using the number of individual cells in said population of contacted test cells that are classified by the classifier and the number of cells in said population of contacted test cells that that are not classified by said classifier.

3. The method of claim 1, wherein the test compound has unknown mode of action.

4. The method of claim 1, wherein said determining employs a Bayesian theorem.

5. The method of claim 1, wherein said set of classifiers comprises at least ten classifiers.

6. The method of claim 1, wherein said cytological attributes include size, staining intensity, shape and texture.

7. The method of claim 1, wherein said obtaining step is done by:
   a) capturing an image of said contacted test cells; and
   b) analyzing said image to provide said values.

8. The method of claim 7, wherein said capturing is done by an automated microscope and said analyzing is done by a computer operably linked to said automated microscope.

9. A microscopy system comprising:
   a) a device for capturing an image of a population of cells; and
   b) a computer, operably linked to said device, comprising programming for:
      i. analyzing said image to provide values for a plurality of cytological attributes of said cells; and
      ii. scoring said cells using said values to provide a likelihood score for at least one of a set of classifiers,
      wherein said set classifiers are defined using values for said cytological attributes obtained from cells that have been contacted with compounds of known mode of action and wherein the likelihood score indicates the likelihood that the values of (b)(i) match a classifier of the set of classifiers.

10. The microscopy system of claim 9, wherein said device is an automated microscope.

11. A method for standardizing an image of cells that are grown in a well of a multi-well culture plate, comprising:
   a) subtracting the median background pixel value of a first image of cells that are:
      i. present in a first well of said multi-well plate; and
      ii. contacted with a test agent, from the pixel values of said first image to provide a second image;

b) dividing the pixel values of said second image by the median foreground pixel values of untreated cells in a second well of said multi-well plate, thereby providing a third image.

12. The method of claim 11, further comprising:
rescaling said third image so that all of the pixels in the third image are above zero.

13. The method of claim 11, further comprising:
repeating said method for images of cells in further wells of said multi-well plate, wherein said further wells comprise cells that have been contacted with further test agents and said method provides further third images.

14. A non-transitory computer readable medium comprising executable instructions for performing the method of claim 11.

15. A method for providing a phenotypic classifier, comprising:
a) contacting a first population of cells with a first compound having a first known mode of action to provide a first population of contacted cells; and
b) contacting a second population of cells with a second compound having a second known mode of action to provide a second population of contacted cells;
c) obtaining values for a plurality of cytological attributes of:
i. said first population of contacted cells,
ii. said second population of contacted cells, and
iii. an untreated population of cells, and
d) identifying ranges of values for each of said cytological attributes that, together, distinguish said first population of contacted cells from said second population of contacted cells and said untreated population of cells.

16. The method of claim 15, further comprising:
contacting a third population of cells with a third compound having a third known mode of action to provide a third population of contacted cells;
obtaining values for said plurality of cytological attributes of said third population of contacted cells; and
identifying ranges of values for each of said cytological attributes that, together, distinguish said first population of contacted cells from said second and third populations of contacted cells and said untreated population of cells.

17. The method of claim 15, wherein said first population of cells and said untreated population of cells are grown in a first multi-well plate, and said method further comprises:
obtaining values for a second untreated population of cells grown on a second multi-well plate; and
identifying ranges of values for each of said cytological attributes that, together, distinguish said first population of contacted cells from said second population of contacted cells, said untreated population of cells grown on the first multi-well plate, and said second untreated population of cells.

18. The method of claim 15, wherein said cytological attributes include size, staining intensity, shape and texture.

19. The method of claim 15, further comprising determining the performance of said classifier by:
a) contacting a third population of cells with said first compound to provide a third population of contacted cells;
b) obtaining values for said plurality of cytological attributes of said third population of contacted cells; and
c) determining if said values for said plurality of cytological attributes of said third population of contacted cells are in the ranges of values that together, distinguish said first population of contacted cells from said second population of contacted cells and said untreated population of cells.

20. The method of claim 15, wherein the phenotypic classifier has improved performance as a classifier compared to a phenotypic classifier provided without using said second untreated population of cells.

* * * * *